US005804392A

United States Patent [19]

Esmon et al.

[11] Patent Number: 5,804,392

[45] Date of Patent: Sep. 8, 1998

[54] DIAGNOSTIC ASSAYS USING SOLUBLE ENDOTHELIAL CELL PROTEIN C/ACTIVATED PROTEIN C RECEPTOR

[75] Inventors: Charles T. Esmon, Oklahoma City; Deborah J. Stearns-Kurosawa; Shinichiro Kurosawa, both of Edmond, all of Okla.

[73] Assignee: Oklahoma Medical Research Foundation, Oklahoma City, Okla.

[21] Appl. No.: 884,203

[22] Filed: Jun. 27, 1997

[51] Int. Cl.[6] ........................ G01N 33/53; G01N 33/564; C07K 16/28

[52] U.S. Cl. ............................ 435/7.1; 435/7.8; 435/975; 436/506; 530/387.1; 530/388.22; 530/389.1

[58] Field of Search ............................ 435/7.1, 7.8, 975; 436/506; 530/387.1, 388.22, 389.1

[56] References Cited

U.S. PATENT DOCUMENTS

| | | | |
|---|---|---|---|
| 4,782,137 | 11/1988 | Hopp et al. . | |
| 5,009,889 | 4/1991 | Taylor et al. . | |
| 5,298,599 | 3/1994 | Rezaie et al. . | |
| 5,695,993 | 12/1997 | Fukudome et al. ..................... | 435/325 |

OTHER PUBLICATIONS

Boehme, et al., "Release of thrombomodulin from endothelial cells by concentrated action of TNF–α and neutrophils: in vivo and in vitro studies," *Immunology* 87:134–140 (1996).

Bourin and Lindahl, "Review Article: Glycosaminoglycans and the regulation of blood coagulation," *Biochem. J.* 289:313–330 (1993).

Conway and Rosenberg, "Tumor Necrosis Factor Suppresses Transcription of the Thrombomodulin Gene in Endothelial Cells," *Mol. Cell. Biol.* 8(12):5588–5592 (1988).

Dahlbäck, "Protein S and C4b–Binding Protein: Components Involved in the Regulation of the Protein C Anticoagulant System," *Thromb. Haemostas.* 66:49–61 (1991).

Dahlbäck, "Inhibition of Protein $C_a$ Cofactor Function of Human and Bovine Protein S by C4b–binding Protein," *J. Biol. Chem.* 261(26):12022–12027 (1986).

Dittman, W. A. "Thrombomodulin—Biology and Potential Cardiovascular Applications," *Trends Cardiovasc. Med.* 1(8):331–336 (1991).

(List continued on next page.)

*Primary Examiner*—David Saunders
*Assistant Examiner*—F. Pierre Vander Vegt
*Attorney, Agent, or Firm*—Arnall Golden & Gregory, LLP

[57] ABSTRACT

Plasma EPCR has been isolated, characterized and shown to block cellular protein C activation and APC anticoagulant activity. Plasma EPCR appears to be about 43,000 daltons and circulates at approximately 100 ng/ml (98.4±27.8 ng/ml, n=22). Plasma EPCR bound activated protein C with an affinity similar to that of recombinant soluble EPCR ($Kd_{app}$ approximately 30 nM), and inhibits both protein C activation on an endothelial cell line and APC anticoagulant activity in a one-stage factor Xa clotting assay. Soluble plasma EPCR appears to attenuate the membrane-bound EPCR augmentation of protein C activation and the anticoagulant function of activated protein C. Soluble EPCR has also been detected in urine. Levels of soluble EPCR can rise in inflammatory disease associated with vascular injury and appear to be correlated with inflammation and disease states associated with abnormal coagulation. Since EPCR expression is restricted to larger vessels and is usually negative in cappillaries, these observations provide a mechanism for analyzing injury/stimulation of large vessel endothelial cells.

11 Claims, 6 Drawing Sheets

OTHER PUBLICATIONS

Dittman and Majerus, "Structure and Function of Thrombomodulin: A Natural Anticoagulant," *Blood* 75(2):329–336 (1990).

Dreyfus et al., "Treatment of Homozygous Protein C Deficiency and Neonatal Purpura Fulminans with a Purified Protein C Concentrate," *N. Engl. J. Med.* 325(22):1565–1568 (1991).

Edgell, et al., "Permanent cell line expressing human factor VIII–related antigen established by hybridization," *Proc. Natl. Acad. Sci.* (*USA*) 80:3734–3737 (1983).

Engelman et al., "Identifying Nonpolar Transbilayer Helices in Amino Acid Sequences of Membrane Proteins," *Annu. Rev. Biophys. Chem.* 15:321–53 (1986).

Esmon, et al., "[21] Protein C Activation," *Methods Enzymol.* 222:359–385 (1993).

Fukudome, et al., "The Endothelial Cell Protein C Receptor—Cell Surface Expression and Direct Ligand Binding by the Soluble Receptor," *J. Biol. Chem.* 271(29):17491–17498 (1996).

Fukudome and Esmon, "Molecular Cloning and Expression of Murine and Bovine Endothelial Cell Protein C/Activated Protein C Receptor (EPCR)—The Structural and Functional Conservation in Human, Bovine and Murine EPCR*," *J. Biol. Chem.* 270(10):5571–5577 (1995).

Fukudome and Esmon, "Identification, Cloning, and Regulation of a Novel Endothelial Cell Protein C/Activated Protein C Receptor*," *J. Biol. Chem.* 269(42):26486–26491 (1994).

Galvin, et al., "Reconstitution of Rabbit Thrombomodulin Into Phospholipid Vesicles," *J. Biol. Chem.* 262(5):2199–2205 (1987).

Gerson et al., "Severe Acquired Protein C Deficiency in Purpura Fulminans Associated with Disseminated Intravascular Coagulation: Treatment with Protein C Concentrate," *Pediatrics* 91(2):418–422 (1993).

Heaney, et al., "Membrane–associated and soluble granylocyte/macrophoage–colony –stimulating factor receptor α submits are independently regulated in HL–60 cells," *Proc. Natl. Acad. Sci. U.S.A.* 92:2365–2369 (1995).

Heaney, ML and DW Golde, "Soluble cytokine receptors," *Blood* 87(3):847–857 (1996).

Hofsteenge, et al., "Effect of thrombomodulin on the kinetics of the interaction of thrombin with substrates and inhibitors," *Biochem. J.* 237:243–251 (1986).

Horiuchi, et al., "Soluble interleukin–6 receptors released from T cell or granulocyte/macrophage cell lines and human peripheral blood mononuclear cells are generated thourgh an alternative splicing mechanism," *Eur. J. Immunol.* 24:1945–1948 (1994).

Ishii and Majerus, "Thrombomodulin is Present in Human Plasma and Urine," *J. Clin. Invest.* 76:2178–2181 (1985).

Jackman, et al., "Human thrombomodulin gene is intron depleted: Nucleic acid sequences of the cDNA and gene predict protein structure and suggest sites of regulatory control," *Proc. Natl. Acad. Sci.* (*USA*) 84:6425–6429 (1987).

Mathews, "Structure of a Nonadecapeptide of the Fifth EGF Domain of Thrombomodulin Complexed with Thrombin," *Biochemistry* 33:13547–13552 (1994).

Moore, et.al., "Tumor Necrosis Factor Leads to the Internalization and Degradation of Thrombosis from the Surface of Bovine Aortic Endothelial Cells in Culture," *Blood* 73(1):159–165 (1989).

Müllberg, et al., "The Soluble Human IL–6 Receptor," *J. Immunol.* 152:4958–4968 (1994).

Ohdama, et al., "Clinical Thrombomodulin in Wegener's Granulomatosis as an Indicator of Vascular Injuries," *Chest* 106:666–671 (1994).

Owen, et al., "The Conversion of Prothrombin to Thrombin," *J. Biol. Chem.* 249(2):594–605 (1974).

Parkinson, et al., "Stable Expression of a Secretable Deletion Mutant of Recombinant Human Thrombomodulin in Mammalian Cells," *J. Biol. Chem.* 265(21):12602–12610 (1990).

Quehenberger, et al., "Increased Levels of Activated Factor VII and Decreased Plasma Protein S Activity and Circulating Thrombomodulin During Use of Oral Contraceptives," *Thromb. Haemost.* 76:729–734 (1996).

Regan, et al., "The Endothelial Cell Protein C Receptor—Inhibition of Activated Protein C Anticoagulant Function without Modulation of Reaction with Proteinase Inhibitors*," *J. Biol. Chem.* 271(29):17499–17503 (1996).

Reitsma, et al., "Protein C Deficiency: A Database of Mutations, 1995 Update," *Thromb. Haemost.* 73:876–879 (1995).

Rezaie, et al., "Communication: Protein C Inhibitor Is a Potent Inhibitor of the Thrombin–Thrombomodulin Complex," *J. Biol. Chem.* 270(43):25336–25339 (1995).

Takahashi, et al., "Circulating Thrombomodulin As a Novel Endothelial Cell Marker: Comparison of Its Behavior with von Willebrand Factor and Tissue Type Plasminogen Activator," *Am. J. Hematol.* 41:32–39 (1992).

Takano, et al., "Plasma Thrombomodulin in Health and Diseases," *Blood.* 76(10):2024–2029 (1990).

Tanaka, et al., "Increased Thrombomodulin Values in Plasma of Diabetic Men with Microangiopathy," *Clin. Chem.* 37(2):269–272 (1991).

Taylor et al., "Protein C Prevents the Coagulopathic and Lethal Effects of *Escherichia coli* Infusion in the Baboon," *J. Clin. Invest.* 79:918–925 (1987).

Taylor et al., "C4b–Binding Protein Exacerbates the Host Response to *Escherichia coli*," *Blood* 78(2):357–363 (1991).

von Heijne, "A New Method for Predicting Signal Sequence Cleavage Sites," *Nucleic Acids Res.* 14(11):4683–4690 (1986).

Wada, et al., "Plasma Thrombomodulin as a Marker of Vascular Disorders in Thrombotic Thrombocytopenic Purpura and Disseminated Intravascular Coagulation," *Am. J. Hematol.* 39:20–24 (1992).

Wen, et al., "Human Thrombomodulin: Complete cDNA Sequence and Chromosome Localization of the Gene," *Biochemistry* 26:4350–4357 (1987).

Ye, et al., "The Fifth and Sixth Growth Factor–like Domains of Thrombomodulin Bind to the Anion–binding Exosite of Thrombin and Alter Its Specificity," *J. Biol. Chem.* 267(16):11023–11028 (1992).

Ye, et al., "The Active Site of Thrombin is Altered Upon Binding to Thrombomodulin—Two Distinct Structural Changes are Detected by Fluorescence, but only one Correlates with Protein C Activation," *J. Biol. Chem.,* 266(34):23016–23021 (1991).

REGULAR SEQUENCE :

```
hum:  S A E N T K G  201
bov:  T T N N L K G
mur:  T T Q N M K G
bab:  S M E N M K G
```

ALTERNATIVE :

```
hum:  M M G R G P G L Q A G E R A G S R Q M D G P E G W M P _ _ R
bov:  M M G S G R D L C V G W V P G K W V _ E L K D G Y L L S N R
mur:  V R G F W P C L C V G E G M T A R Q M K G H E G S L _ E Q Q
bab:  M M G L G P R P _ A S W G E G G V Q T N G W T *

hum:  A T R G P Q L G V W D R T H A A S V S W *
bov:  R P R A G D L G L S T H I L C E L V N *
mur:  K E E A G D S G E G T S T K P K S L G D V L *
```

NEW CARBOXYL - TERMINAL :

human: 48 residues
bovine: 48 residues
murine: 51 residues
baboon: 22 residues

FIG. 3

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1302 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: misc_feature
( B ) LOCATION: 1..1302
( D ) OTHER INFORMATION: /note= "Nucleotides 25 through 738 encode the Endothelial Cell Protein Receptor of Sequence ID No. 2."

( x i ) SEQUENCE DESCRIPTION: SEQ ID NO:1:

CAGGTCCGGA GCCTCAACTT CAGGATGTTG ACAACATTGC TGCCGATACT GCTGCTGTCT 60

GGCTGGGCCT TTTGTAGCCA AGACGCCTCA GATGGCCTCC AAAGACTTCA TATGCTCCAG 120

ATCTCCTACT TCCGCGACCC CTATCACGTG TGGTACCAGG GCAACGCGTC GCTGGGGGGA 180

CACCTAACGC ACGTGCTGGA AGGCCCAGAC ACCAACACCA CGATCATTCA GCTGCAGCCC 240

TTGCAGGAGC CCGAGAGCTG GGCGCGCACG CAGAGTGGCC TGCAGTCCTA CCTGCTCCAG 300

TTCCACGGCC TCGTGCGCCT GGTGCACCAG GAGCGGACCT TGGCCTTTCC TCTGACCATC 360

CGCTGCTTCC TGGGCTGTGA GCTGCCTCCC GAGGGCTCTA GAGCCCATGT CTTCTTCGAA 420

GTGGCTGTGA ATGGGAGCTC CTTTGTGAGT TTCCGGCCGG AGAGAGCCTT GTGGCAGGCA 480

GACACCCAGG TCACCTCCGG AGTGGTCACC TTCACCCTGC AGCAGCTCAA TGCCTACAAC 540

CGCACTCGGT ATGAACTGCG GGAATTCCTG GAGGACACCT GTGTGCAGTA TGTGCAGAAA 600

CATATTTCCG CGGAAAACAC GAAAGGGAGC CAAACAAGCC GCTCCTACAC TTCGCTGGTC 660

CTGGGCGTCC TGGTGGGCGG TTTCATCATT GCTGGTGTGG CTGTAGGCAT CTTCCTGTGC 720

ACAGGTGGAC GGCGATGTTA ATTACTCTCC AGCCCCGTCA GAAGGGGCTG GATTGATGGA 780

GGCTGGCAAG GGAAAGTTTC AGCTCACTGT GAAGCCAGAC TCCCCAACTG AAACACCAGA 840

AGGTTTGGAG TGACAGCTCC TTTCTTCTCC CACATCTGCC CACTGAAGAT TTGAGGGAGG 900

GGAGATGGAG AGGAGAGGTG GACAAAGTAC TTGGTTTGCT AAGAACCTAA GAACGTGTAT 960

GCTTTGCTGA ATTAGTCTGA TAAGTGAATG TTTATCTATC TTTGTGGAAA ACAGATAATG 1020

GAGTTGGGGC AGGAAGCCTA TGCGCCATCC TCCAAAGACA GACAGAATCA CCTGAGGCGT 1080

TCAAAAGATA TAACCAAATA AACAAGTCAT CCACAATCAA AATACAACAT TCAATACTTC 1140

CAGGTGTGTC AGACTTGGGA TGGGACGCTG ATATAATAGG GTAGAAAGAA GTAACACGAA 1200

GAAGTGGTGG AAATGTAAAA TCCAAGTCAT ATGGCAGTGA TCAATTATTA ATCAATTAAT 1260

AATATTAATA AATTTCTTAT ATTTAAAAAA AAAAAAAAAA AA 1302

( 2 ) INFORMATION FOR SEQ ID NO:2:

( i ) SEQUENCE CHARACTERISTICS:
( A ) LENGTH: 238 amino acids
( B ) TYPE: amino acid
( D ) TOPOLOGY: linear ( i i ) MOLECULE TYPE: protein ( i i i ) HYPOTHETICAL: NO ( i x ) FEATURE:
( A ) NAME/KEY: misc_feature
( B ) LOCATION: 1..365

( D ) OTHER INFORMATION: /note= "Endothelial Cell Protein Receptor encoded by nucleotides 1 through 1302 of Sequence ID No. 1."

( i x ) FEATURE:
( A ) NAME/KEY: Modified-site
( B ) LOCATION: 1..15
( D ) OTHER INFORMATION: /note= "Amino acids 1-15 represent a putative signal sequence."

( i x ) FEATURE:
( A ) NAME/KEY: Domain
( B ) LOCATION: 211..236
( D ) OTHER INFORMATION: /note= "Amino acids 211-236 represent a putative transmembrane domain."

( i x ) FEATURE:
( A ) NAME/KEY: Active-site
( B ) LOCATION: 47..174
( D ) OTHER INFORMATION: /note= "Amino acids 47-49, 64-66, 136-138 and 172-174 represent potential N- glycosylation sites."

( i x ) FEATURE:
( A ) NAME/KEY: Active-site
( B ) LOCATION: Cys 17
( D ) OTHER INFORMATION: /note=immediately preceeds amino acid cleavage site ( i x ) FEATURE:
( A ) NAME/KEY: Active-site
( B ) LOCATION: Gly 201
( D ) OTHER INFORMATION: /note=peptide inserts in alternatively spliced EPCR ( i x ) FEATURE:
( A ) NAME/KEY: Modified-site
( B ) LOCATION: 17..186
( D ) OTHER INFORMATION: /note= "Amino acids 17, 114, 118 and 186 represent extracellular cysteine residues."

( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Leu | Thr | Thr | Leu | Leu | Pro | Ile | Leu | Leu | Leu | Ser | Gly | Trp | Ala | Phe |
| 1 | | | | 5 | | | | | 10 | | | | | 15 | |
| Cys | Ser | Gln | Asp | Ala | Ser | Asp | Gly | Leu | Gln | Arg | Leu | His | Met | Leu | Gln |
| | | | 20 | | | | | 25 | | | | | 30 | | |
| Ile | Ser | Tyr | Phe | Arg | Asp | Pro | Tyr | His | Val | Trp | Tyr | Gln | Gly | Asn | Ala |
| | | 35 | | | | | 40 | | | | | 45 | | | |
| Ser | Leu | Gly | Gly | His | Leu | Thr | His | Val | Leu | Glu | Gly | Pro | Asp | Thr | Asn |
| | 50 | | | | | 55 | | | | | 60 | | | | |
| Thr | Thr | Ile | Ile | Gln | Leu | Gln | Pro | Leu | Gln | Glu | Pro | Glu | Ser | Trp | Ala |
| 65 | | | | | 70 | | | | | 75 | | | | | 80 |
| Arg | Thr | Gln | Ser | Gly | Leu | Gln | Ser | Tyr | Leu | Leu | Gln | Phe | His | Gly | Leu |
| | | | | 85 | | | | | 90 | | | | | 95 | |
| Val | Arg | Leu | Val | His | Gln | Glu | Arg | Thr | Leu | Ala | Phe | Pro | Leu | Thr | Ile |
| | | | 100 | | | | | 105 | | | | | 110 | | |
| Arg | Cys | Phe | Leu | Gly | Cys | Glu | Leu | Pro | Pro | Glu | Gly | Ser | Arg | Ala | His |
| | | 115 | | | | | 120 | | | | | 125 | | | |
| Val | Phe | Phe | Glu | Val | Ala | Val | Asn | Gly | Ser | Ser | Phe | Val | Ser | Phe | Arg |
| | 130 | | | | | 135 | | | | | 140 | | | | |
| Pro | Glu | Arg | Ala | Leu | Trp | Gln | Ala | Asp | Thr | Gln | Val | Thr | Ser | Gly | Val |
| 145 | | | | | 150 | | | | | 155 | | | | | 160 |
| Val | Thr | Phe | Thr | Leu | Gln | Gln | Leu | Asn | Ala | Tyr | Asn | Arg | Thr | Arg | Tyr |
| | | | | 165 | | | | | 170 | | | | | 175 | |
| Glu | Leu | Arg | Glu | Phe | Leu | Glu | Asp | Thr | Cys | Val | Gln | Tyr | Val | Gln | Lys |
| | | | 180 | | | | | 185 | | | | | 190 | | |
| His | Ile | Ser | Ala | Glu | Asn | Thr | Lys | Gly | Ser | Gln | Thr | Ser | Arg | Ser | Tyr |

195 200 205

Thr Ser Leu Val Leu Gly Val Leu Val Gly Gly Phe Ile Ile Ala Gly
210 215 220

Val Ala Val Gly Ile Phe Leu Cys Thr Gly Gly Arg Arg Cys
225 230 235

( 2 ) INFORMATION FOR SEQ ID NO:3:

( i ) SEQUENCE CHARACTERISTICS:
( A ) LENGTH: 48 amino acids
( B ) TYPE: amino acid
( D ) TOPOLOGY: linear ( i i ) MOLECULE TYPE: protein ( i i i ) HYPOTHETICAL: NO ( x i ) SEQUENCE DESCRIPTION: SEQ ID NO:3:

Met Met Gly Arg Gly Pro Gly Lys Gln Ala Gly Glu Arg Ala Gly Ser
1 5 10 15

Arg Gln Met Asp Gly Pro Glu Gly Trp Met Pro Arg Ala Thr Arg Gly
20 25 30

Pro Gln Lys Gly Val Trp Asp Arg Thr His Ala Ala Ser Val Ser Trp
35 40 45

( 2 ) INFORMATION FOR SEQ ID NO:4:

( i ) SEQUENCE CHARACTERISTICS:
( A ) LENGTH: 148 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

ATGATGGGAC GGGGCCCAGG CCTGCAAGCT GGGGAGAGGG CGGGTTCCAG ACAAATGGAT 60

GGACCTGAAG GATGGATGCC TAGAGCAACA AGAGGCCCAC AGCTGGGGGT TTGGGACAGA 120

ACACACGCAG CTTCAGTCAG TTGGTAAA 148

( 2 ) INFORMATION FOR SEQ ID NO:5:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: misc_feature
( B ) LOCATION: 1..24
( D ) OTHER INFORMATION: /note= "5'sense primer near end of exon II."

( x i ) SEQUENCE DESCRIPTION: SEQ ID NO:5:

TCGTGCGCCT GGTGCACCAG GAGC 24

-continued ( 2 ) INFORMATION FOR SEQ ID NO:6:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: misc_feature
( B ) LOCATION: 1..24
( D ) OTHER INFORMATION: /note= "3'antisense primer within exon IV."

( x i ) SEQUENCE DESCRIPTION: SEQ ID NO:6:

CGCCGTCCAC CTGTGCACAG GAAG 24

( 2 ) INFORMATION FOR SEQ ID NO:7:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: misc_feature
( B ) LOCATION: 1..22
( D ) OTHER INFORMATION: /note= "5'sense primer near end of exon III."

( x i ) SEQUENCE DESCRIPTION: SEQ ID NO:7:

AGCAGCTCAA TGCCTACAAC CG 22

( 2 ) INFORMATION FOR SEQ ID NO:8:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: misc_feature
( B ) LOCATION: 1..29
( D ) OTHER INFORMATION: /note= "3'antisense primer within exon IV."

( x i ) SEQUENCE DESCRIPTION: SEQ ID NO:8:

CCGTAGAAGG ACACGTGTCC ACCTGCCGC 29

DIAGNOSTIC ASSAYS USING SOLUBLE ENDOTHELIAL CELL PROTEIN C/ ACTIVATED PROTEIN C RECEPTOR

The United States government has certain rights in this invention by virtue of national Institutes of Health grant PO1HL 54804 to Charles T. Esmon.

BACKGROUND OF THE INVENTION

The present invention is generally in the area of assays involving detection and/or measurement of endothelial cell protein C/activated protein C receptor or soluble forms thereof derived either by proteolysis or by alternative splicing.

The activation of protein C to its active serine protease, activated protein C (APC), initiates a series of events that play a key role in the regulation of blood coagulation. The clinical importance of the protein C pathway is evidenced by the multitude of dysfunctions in this pathway that result in thrombosis (Esmon and Schwarz. 1995. *Trends Cardiovasc. Med.* 5:141–148; Reitsma, et al. 1995. *Thromb. Haemost.* 73:876–879). Patients deficient in protein C usually exhibit life threatening thrombotic-complications in infancy (Seligsohn et al., 1984. *N. Engi. J. Med.* 310, 559–562; Esmon, 1992. *Trends Cardiovasc. Med.* 2, 214–220) that are corrected by protein C administration (Dreyfus et al., 1991. *N. Engl. J. Med.* 325, 1565–1568).

Protein C and APC have also been implicated in the regulation of the host response to inflammation. Activated protein C (APC) can prevent the lethal effects of *E. coli* in baboon models of gram negative sepsis (Taylor et al., 1987. *J. Clin. Invest.* 79; U.S. Pat. No. 5,009,889 to Taylor and Esmon) and preliminary clinical results suggest that protein C is effective in treating certain forms of human septic shock (Gerson et al., 1993. *Pediatrics* 91, 418–422). Inhibition of protein S, an important component of the protein C pathway, exacerbates the response of primates to sublethal levels of *E. coli* and augments the appearance of TNF in the circulation (Taylor et al., 1991. *Blood* 78, 357–363). These results suggest that protein C may both control coagulation and influence inflammation.

Protein C is activated when thrombin, the terminal enzyme of the coagulation system, binds to an endothelial cell surface protein, thrombomodulin (Esmon, 1989. *J. Biol. Chem.* 264, 4743–4746; Dittman and Majerus, 1990. *Blood* 75, 329–336; Dittman, 1991. *Trends Cardiovasc. Med.* 1, 331–336). In cell culture, thrombomodulin transcription is blocked by exposure of endothelial cells to tumor necrosis factor (TNF) (Conway and Rosenberg, 1988. *Mol. Cell. Biol.* 8, 5588–5592) and thrombomodulin activity and antigen are subsequently internalized and degraded (Lentz et al., 1991. *Blood* 77, 543–550, Moore, et.al., 1989. *Blood* 73, 159–165). C4bBP, a regulatory protein of the complement system, binds protein S to form a complex that is functionally inactive in supporting APC anticoagulant activity in vitro (Dahlbäck, 1986. *J. Biol. Chem.* 261, 12022–12027) and in vivo (Taylor,et al., 1991). C4bBP behaves as an acute phase reactant (Dahlbäck, 1991. *Thromb. Haemostas.* 66, 49–61). Thus, proteins of this pathway not only appear to regulate inflammation, but they also interact with components that regulate inflammation, and they themselves are subject to down regulation by inflammatory mediators.

Endothelial cells play a critical role in the protein C pathway in that they express two of the known receptors responsible for efficient protein C activation, thrombomodulin and the endothelial protein C/APC receptor (EPCR) (Fukudome and Esmon. 1994. *J. Biol. Chem.* 269:26486–26491; Stearns-Kurosawa, et al. 1996. *Proc. Natl. Acad. Sci.* (*USA*) 93:10212–10216). Thrombomodulin (CD141) is a transmembrane cofactor that binds circulating thrombin with high affinity and the resultant enzyme-cofactor complex is required for physiologically relevant protein C activation rates (Esmon and Owen. 1981. *Proc. Natl. Acad. Sci.* (*USA*) 78:2249–2252; Dittman, W. A. 1991. *Trends Cardiovasc. Med.* 1:331–336).

EPCR is a recently identified receptor with significant homology to the CD1/MHC class 1 family (Fukudome and Esmon, 1994; Fukudome, et al. 1996. *J. Biol. Chem.* 271:17491–17498; Regan, et al. 1996. *J. Biol. Chem.* 271:17499–17503). The cloning and biological role of the endothelial cell receptor for protein C was described in PCT/US95/09636 by Oklahoma Medical Research Foundation, entitled "Cloning and Regulation of an Endothelial Cell Protein C/Activated Protein C Receptor". The protein was predicted to consist of 238 amino acids, which includes a 15 amino acid signal sequence at the N-terminus, and a 23 amino acid transmembrane region which characterizes the receptor as a type 1 transmembrane protein.

EPCR binds both protein C and APC with similar affinity ($Kd_{app}$~30 nM) (Fukudome, et al., 1996) in the presence of calcium and facilitates protein C activation by presenting the protein C substrate to the thrombin-thrombomodulin activation complex on cell surfaces (Stearns-Kurosawa, et al., 1996). Both endothelial cell receptors are type 1 transmembrane proteins in which the ligand binds to an extracellular domain and both have a short intracellular cytoplasmic tail (Fukudome, et al. 1996; Jackman, et al. 1987. *Proc. Natl. Acad. Sci.* (*USA*) 84:6425–6429; Wen, et al., 1987. *Biochemistry* 26:4350–4357; Suzuki, et al. 1987. *EMBO J.* 6:1891–1897). In addition, their in vitro cell surface expression is down-regulated similarly by tumor necrosis factor-α (Fukudome and Esmon 1994). However, the characteristics of soluble forms of thrombomodulin and EPCR differ in several respects. Recombinant soluble thrombomodulin has reduced cofactor activity relative to the membrane form (Galvin, et al. 1987. *J. Biol. Chem.* 262:2199–2205; Parkinson, et al. 1990. *J. Biol. Chem.* 265:12602–12610). With both purified components and with cells, the changes in thrombin's substrate specifically induced by thrombomodulin result from competition for a shared binding domain on thrombin as well as conformational alterations in the active site pocket (Ye, et al. 1991. *J. Biol. Chem.* 266:23016–23021; Lu, et al. 1989. *J. Biol. Chem.* 264:12956–12962; Ye, et al. 1992. *J. Biol. Chem.* 267:11023–11028; Hofsteenge, et al. 1986. *Biochem. J.* 237:243–251; Mathews, 1994. *Biochemistry* 33:13547–13552; Esmon, et al. 1982. *J. Biol. Chem.* 257:7944–7947; Sadler, et al. 1993. *Haemostasis* 23:183–193). Soluble thrombomodulin also accelerates inactivation of thrombin by a variety of inhibitors (Bourin and Lindahl. 1993. *Biochem. J.* 289:313–330; Rezaie, 1995. *J. Biol. Chem.* 270:25336–25339). Both plasma and urine contain detectable thrombomodulin (Takano, et al. 1990. *Blood.* 76:2024–2029; Ishii and Majerus. 1985. *J. Clin. Invest.* 76:2178–2181) and because the thrombomodulin gene does not contain introns (Jackman, et al., 1987), these soluble forms are due to proteolysis of the extracellular domain at the cell surface.

Soluble degradation products of thrombomodulin in plasma are a known marker of endothelial cell damage in a variety of disease states (Takano, et al., 1990; Tanaka, et al. 1991. *Clin. Chem.* 37:269–272; Takahashi, et al. 1991. *Am. J. Hematol.* 38:174–177; Asakura, et al. 1991. *Am. J. Hema-*

*tol.* 38:281–287; Wada, et al. 1992. *Am. J. Hematol.* 39:20–24; Takahashi, et al. 1992. *Am. J. Hematol.* 41:32–39; Ohdama, et al. 1994. *Chest* 106:666–671) and are comprised of a mixture of thrombin-binding fragments with varying reduced affinities, as well as non-binding fragments (Takano, et al., 1990).

In contrast, recombinant soluble EPCR (rsEPCR), truncated just before the transmembrane domain, binds both protein C and APC with an affinity similar to that observed for intact cell-surface expressed EPCR (Fukudome, et al. 1996). APC anticoagulant activity is inhibited effectively when bound to rsEPCR (Regan, et al., 1996), presumably because both rsEPCR and factor Va share binding determinants in a groove reminiscent of the anion binding exosite I in thrombin occupied by thrombomodulin (Mather, et al. 1996. *EMBO J.* 15:6822–6831). However, rsEPCR does not appear to influence proteolysis of small synthetic substrates by APC, nor inactivation of APC by α1-antitrypsin or protein C inhibitor (Regan, et al., 1996). Unlike membrane-bound EPCR which enhances protein C activation (Stearns-Kurosaw, at al., 1996), rsEPCR has little effect on protein C activation by the soluble thrombin-thrombomodulin complex (Regan, et al., 1996), suggesting that any soluble forms of EPCR might inhibit protein C activation by competing with membrane-associated EPCR for protein C.

Immunohistochemistry indicates that EPCR is present primarily on the surface of endothelial cells from large vessels and is absent or present at low levels on most capillary endothelial cells.

It is therefore an object of the present invention to identify therapeutic and diagnostic uses for naturally occurring soluble EPCR.

It is a further object of the present invention to characterize naturally occurring soluble EPCR.

SUMMARY OF THE INVENTION

Plasma EPCR (has been isolated, characterized and shown to block cellular protein C activation and APC anticoagulant activity. Plasma EPCR appears to be about 43,000 daltons and circulates at approximately 100 ng/ml (98.4±27.8 ng/ml, n=22). Plasma EPCR was purified from human citrated plasma using ion-exchange, immunoaffinity, and protein C affinity chromatography. Flow cytometry experiments demonstrated that plasma EPCR bound activated protein C with an affinity similar to that previously determined from recombinant truncated EPCR ($Kd_{app}$ approximately 30 nM), defined as EPCR not including the transmembrane and cytoplasmic domains. Furthermore, plasma EPCR inhibited both protein C activation on an endothelial cell line and APC anticoagulant activity in a one-stage factor Xa clotting assay. Soluble EPCR has also been detected in human urine. Cloning of the gene encoding EPCR demonstrates that at least human EPCR can be alternatively spliced, yielding a truncated soluble EPCR including an insert unique to the alternatively spliced form (sEPCR). These results indicate that plasma EPCR can be derived either by proteolysis at the cell surface or by alternative splicing.

If the local concentrations of plasma EPCR are sufficiently high, particularly in disease states, the data indicates that the truncated soluble plasma EPCR could attenuate the membrane-bound EPCR augmentation of protein C activation and the anticoagulant function of activated protein C. As demonstrated by the examples comparing normal plasma EPCR with levels of EPCR from patients with an autoimmune disease (systemic lupus erythematosus, SLE) and sepsis (a disorder involving both inflammation and coagulation abnormalities), levels of soluble EPCR appear to be correlated with inflammation and disease states associated with abnormal coagulation. Assays are described based on measurement of soluble EPCR which are indicative of disease conditions involving coagulation, inflammation, and large vessel disease. Assay reagents are described, including isolated purified soluble EPCR, recombinant truncated soluble EPCR, and antibodies to the soluble EPCRs.

BRIEF DESCRIPTION OF THE DRAWINGS

FIG. 3 shows the sequence inserted into human, bovine, murine, and baboon EPCR by alternative splicing.

In FIG. 4*b*, EA.hy926 cell monolayers were pre-incubated for 15 minutes at room temperature with 0.1 μM protein C alone (□) or with 1 μM rsEPCR (●), or 2 μg/ml 1494 mAb (○). Protein C activation was initiated by the addition of thrombin (2 nM final) and the reactions were stopped at the indicated times. Activated protein C was determined with an amidolytic assay and the activity rates in mOD/min are plotted for each time point. Control wells without added thrombin were included (■). Each data point represents the average of triplicate well determinations. In FIG. 4*c*, EA.hy926 cell monolayers were pre-incubated for 15 minutes at room temperature with 0.1 μM protein C and the indicated concentrations of plasma EPCR (○) or rsEPCR (●). Thrombin (final 2 nM) was added and the activation proceeded for 60 minutes at room temperature. The supernatants were added to a mixture of antithrombin and heparin and activated protein C activities (mOD/min) were determined with an amidolytic assay. Each data point represents the average of triplicate well determinations.

DETAILED DESCRIPTION OF THE INVENTION

Definitions

Figure 1:
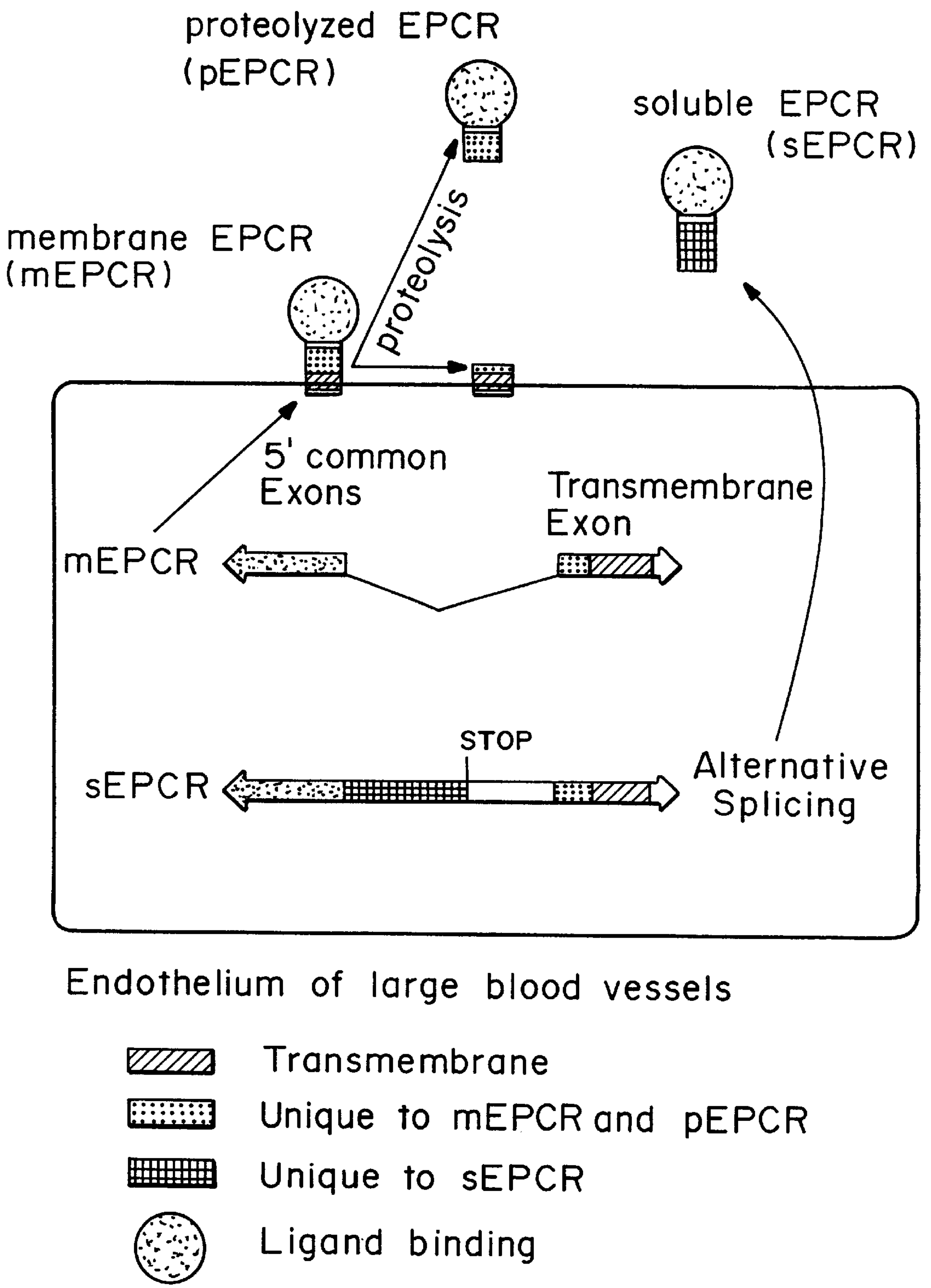
FIG. 1 is a schematic of the two known mechanisms for producing a soluble receptor as applied to EPCR, by proteolysis of the membrane-bound receptor to release an extracellular domain and leave the membrane anchor behind, and by alternative splicing of the mRNA, showing the sequences unique to membrane bound EPCR (mEPCR) and to proteolyzed plasma EPCR (pEPCR), and the sequence unique to soluble EPCR (sEPCR).

Endothelial Protein C Receptor, EPCR.

Soluble, in solution and not bound to a cell surface.

Truncated, not including the transmembrane and cytoplasmic domains; can be a result of either proteolysis or alternative splicing.

Detection and Characterization of Soluble EPCR; Physiological Role and Utility as a Marker Previous investigations into the function of EPCR found that protein C binding to the membrane form of EPCR resulted in facilitation of protein C activation by the thrombin-thrombomodulin complex on cell surfaces (Stearns-Kurosawa, et al., 1996), but that soluble recombinant EPCR inhibited APC anticoagulant activity (Regan, et al. 1996). These observations, along with the knowledge that soluble thrombomodulin degradation products in plasma are a marker of endothelial damage in various disease states, led to the question of whether a soluble circulating form(s) of EPCR existed and, if so, what role it may have in the protein C pathway.

The examples demonstrate that a soluble form of EPCR circulates in plasma and is present in urine. In a healthy donor population, the plasma EPCR level was about 100 ng/ml and it appeared to be a single antigen species of approximately 43,000 daltons. Subsequent purification of the soluble EPCR from plasma and functional studies determined that it was capable of binding both protein C and APC with an affinity similar to intact membrane-bound EPCR. The in vitro studies using an endothelial cell line demonstrated that plasma EPCR inhibited protein C activation at near physiological concentrations of protein C and thrombin. In addition, direct addition of purified plasma EPCR to plasma resulted in inhibition of APC anticoagulant activity that was reversed with monoclonal antibodies to rsEPCR.

The identification of the purified plasma protein as being EPCR was based on comparison with the properties of rsEPCR. These proteins both reacted with the same battery of monoclonal and polyclonal antibodies, had the same amino-terminal sequence, bound to immobilized protein C in a $Ca^{2+}$-dependent fashion, and blocked protein C activation and APC anticoagulant activity with similar dose response curves. In addition, the affinities of both protein C and APC for rsEPCR and plasma EPCR are similar to the affinity of intact membrane-bound EPCR. These properties appear to be unique to EPCR.

Previous studies demonstrated that membrane-bound EPCR expressed on endothelial cells augments protein C activation by a factor of between three and five fold, whereas the examples demonstrate that the soluble form of EPCR purified from plasma inhibits protein C activation on endothelial cells and APC anticoagulant activity. This predicts that EPCR could modulate the protein C pathway in several ways. First, in the larger vessels where thrombomodulin concentration is low to the microcirculation, EPCR expression is correspondingly increased (Laszik, et al., Circulation 1997). Immunohistochemistry shows that in most organs, EPCR expression is most intense on large vessels and decreases progressively with decreasing vessel size, with little or no expression in the most abundant endothelial cell type, the capillary endothelium. EPCR expression may play a critical role in capturing the protein C substrate from the circulation and presenting it to the thrombin-thrombomodulin complex for activation. This is supported by in vitro observations that both the EA.hy926 endothelial cell line and human umbilical vein endothelial cells have at least six times more surface-expressed EPCR antigen than thrombomodulin. In the microcirculation where thrombomodulin concentration is high and EPCR is low, one would predict little influence on protein C activation. Finally, circulating soluble EPCR may reduce the generation of APC and the ability of APC to inactivate factor Va.

In a healthy individual, the soluble EPCR levels are about 2.5 nM, a concentration well below both the $Kd_{app}$ (approximately 30 nM) and the 80 nM protein C concentration in the circulation. Both of the effects of soluble plasma EPCR (inhibition of APC anticoagulant activity and protein C activation) required considerably higher concentrations than that present in normal plasma, leaving the question of the physiological role of the plasma EPCR uncertain. Patients with soluble EPCR levels that exceed 40 nM have been identified, as described in Example 3 (lupus). Thus, if the local concentration near the endothelial cell surface exceeds the systemic concentration, the soluble EPCR concentration would reach levels that would attenuate both APC generation and activity, contributing to thrombotic risk.

A soluble form of a receptor can be produced by proteolytic cleavage of the membrane-bound receptor or by alternative splicing mechanisms. Proteolysis at the membrane surface releases soluble thrombomodulin, and receptors for TNF, IL-1, IL-2, M-CSF, PDGF, and NGF (Heaney, et al. 1996. *Blood* 87:847–857). Soluble receptors have a multitude of potential functions including acting as antagonists of the membrane receptor, stabilizing the ligand, initiating ligand-mediated signaling, downmodulation of the membrane form, and binding to receptor inhibitors to indirectly facilitate receptor-ligand activity. The latter mechanism is used by the IL-1 receptor system in which the soluble isoforms of both IL-1 receptors are generated by proteolytic cleavage and tightly regulate the responsiveness to IL-1$\alpha$ and IL-1$\beta$ (Arend, et al. 1994. *J. Immunol.* 153:4766–4774). The EPCR genomic structure contains an alternative splicing site which would code for a soluble protein truncated just before the transmembrane domain (Fukudome and Esmon. 1995. *J. Biol. Chem.* 270:5571–5577), as discussed below. Soluble IL-6 receptors appear to be generated by both proteolytic and alternative splicing mechanisms (Mullberg, et al. 1994. *J. Immunol.* 152:4958–4968; Lust, et al. 1992. Cytokine 4:96–100; Horiuchi, et al. 1994. *Eur. J. Immunol.* 24:1945–1948). This cleavage site can also be useful in recovering large quantities of soluble EPCR, by constructing an expression vector encoding the truncated EPCR immediately followed by a peptide sequence to which an antibody is specifically directed, as described in U.S. Pat. No. 5,298,599 to Morrissey and Esmon, the teachings of which are incorporated herein. The epitope will then be cleaved by proteolysis, before or after administration to a patient. See also U.S. Pat. No. 4,782,137 to Hopp et al.

Immunohistochemical studies have indicated that EPCR is located primarily on endothelium of large vessels and is barely detectable in capillaries. Plasma EPCR derived from membrane-bound EPCR, can therefore serve as a marker of large vessel disease processes. Plasma EPCR may serve as a useful comparison with plasma thrombomodulin levels which have been shown to be modulated in a variety of disease states, but which would reflect both large and small vessel disease processes, but probably would be dominated by small vessel contributions since most endothelium is microvascular.

Nucleotide and Predicted Protein Structure Analysis of EPCR

The cDNA for EPCR is predicted to code for a protein of 238 amino acids (Sequence ID No. 2), which includes a 15 amino acid signal sequence (von Heijne, (1986) *Nucleic Acids Res*. 14, 4683–4690) at the N-terminal. Therefore, the mature protein is predicted to contain 223 amino acids. Direct sequencing of the recombinant protein showed that the mature protein started at Ser18. Sequence ID No. 2 is the predicted amino acid sequence of EPCR. Amino acids 1–15 of Sequence ID No. 2 (MLTTLLPILLLSGWA) are the putative signal sequence determined by the method of von Heijne (von Heijne, 1986). Amino acids 211–236 of Sequence ID No. 2 (LVLGVLVGGFIIAGVAVGIFLCTGGR) are the putative transmembrane domain. Potential N-glycosylation sites are present at amino acids 47–49, 64–66, 136–138, and 172–174 of Sequence ID No. 2. Extracellular cysteine residues are present at amino acids 17 (removed in plasma EPCR), 114, 118, and 186 of Sequence ID No. 2. A potential transmembrane region (Engelman et al., (1986) *Annu. Rev. Biophys. Chem*. 15, 321–53) consisting of 23 amino acids was identified at the C-terminal end (beginning at amino acid 211 of Sequence ID No. 2).

The protein is a type 1 transmembrane protein. The extracellular domain contains four potential N-glycosylation sites and three Cys residues. Glycosylation is not essential for activity, as shown by N-glycanase digestion. The cytoplasmic region contains only three amino acids and terminates with a Cys, which is palmitoylated. If the terminal cysteine is not properly palmitoylated, the protein may be secreted. Altering the sequence of the EPCR to replace this cysteine with another amino acid thereby provides a means for making an essentially full length EPCR which is secreted instead of being membrane bound.

As used herein, the nucleotide sequences encoding the receptor include the sequence shown in Sequence ID No. 1, and sequences having conservative substitutions, additions or deletions thereof which hybridize to Sequence ID No. 1 under stringent conditions. As used herein, the amino acids sequences constituting the receptor include the sequence shown in Sequence ID No. 2, and sequences having conservative substitutions, additions or deletions thereof which form a receptor having functionally equivalent biological activity. It is well known to those skilled in the art what constitutes conservative substitutions, additions or deletions, and which could be readily ascertained as encoding, or forming, a functionally equivalent receptor molecule using the functional assays described herein. This is further illustrated by reference to FIG. 3, discussed below.

Alternative Splicing

Receptors are most often visualized as being proteins anchored in a cell membrane with the portion exposed to the outside of a cell responsible for binding a specific ligand to generate a physiological response. In many cases, a soluble form of the receptor exists that frequently is quite capable of binding its ligand, despite the fact that it is no longer restricted to a cell. Ligand binding to the soluble receptor isoform can also generate a response which takes many forms, including up- or down-modulation of the membrane-bound receptor interactions, or propagating a response by transporting the ligand to a cell that normally is not responsive (Heaney, ML and DW Golde. Soluble cytokine receptors. *Blood* 87:847–857, 1996).

There are two known mechanisms for producing a soluble receptor: by proteolysis of the membrane-bound receptor to release an extracellular domain and leave the membrane anchor behind, and by alternative splicing of the mRNA (FIG. 1). The latter mechanism can take many forms, but the simplest is when the reading frame continues through an exon-intron boundary and terminates with a stop codon before reaching the sequence coding for the transmembrance anchor. This creates a protein that is similar to the membrane form, but with important differences. It is made, and secreted, as a soluble protein and will have a unique carboxyl-terminal tail. This tail was formed by reading a portion of the intron mRNA sequence that is ignored in the formation of the membrane-bound receptor. Generation of a soluble receptor by alternative splicing can also be modulated independently from the membrane-bound receptor, despite the fact that they both originate from the same mRNA template (Heaney, et al. *Proc. Natl. Acad. Sci. U.S.A*. 92:2365–2369, 1995).

To demonstrate that a soluble receptor is generated by alternative splicing mechanisms, one must know the genomic sequence and intron-exon boundaries of the relevant region. It is also helpful to link the soluble receptor with a physiological response to distinguish it from aberrant mRNA splicing, found fairly frequently including during expression of the protein C and protein S genes (Berg, et al. *Blood Coag Fibrinol*. 7:625–631, 1996).

Details of the following studies and results are described in the examples. Human plasma contains about 100 ng/ml of soluble EPCR (Table 1). This was measured by an enzyme linked immunoassay (ELISA) using two monoclonal antibodies (1494 mAb and 1495 mAb) and standard techniques. Significantly elevated soluble EPCR levels were found in patients with systemic lupus erythematosus and sepsis. These levels seemed fairly high for a membrane-bound receptor that is present, with few exceptions, only on the surface of the large blood vessels. To put this in perspective, thrombomodulin (TM) is expressed on all endothelium, as well as some non-vascular cells, yet normal soluble TM levels are only about 10–40 ng/ml (Takano, et al., *Blood* 76:2024–2029, 1990). The soluble TM levels were elevated in the patients with lupus, but not sepsis. Importantly, there was no correlation between the plasma EPCR and TM levels in these patient groups ($r^2$=0.028 and 0.034, respectively).

TABLE 1

Plasma soluble receptor levels

| | Plasma EPCR ng/ml | Plasma TM ng/ml |
|---|---|---|
| Normal volunteers, n = 20 | 133.4 ± 53.4 | 35.5 ± 20.4 |
| Systemic lupus erythematosus, n = 40 | 262.1 ± 154.5* (P = 0.0004) | 104.7 ± 77.5* (P = 0.0008) |
| Sepsis, n = 24 | 224.9 ± 74.5* (P = 0.00009) | 39.9 ± 73.1 |

*Significant difference between the means relative to normal; unpaired Student's t test.

The TM genomic structure does not contain introns (Jackman, et al. *Proc. Natl. Acad. Sci.* (*USA*) 84:6425–6429, 1987), so the only way to create a soluble TM isoform is by proteolysis of the membrane-bound receptor. Proteolysis of endothelial TM by neutrophil elastase and cathepsin G has been shown in vitro, suggesting that the elevated soluble TM levels found in a variety of disease states result from proteolysis mediated by products of activated inflammatory cells at the endothelial surface (Boehme, et al., *Immunology* 87:134–140, 1996 and Abe, et al. *J. Lab. Clin. Med.* 123:874–881, 1994).

The lack of correlation between the plasma EPCR and TM levels and the high plasma EPCR concentration is consistent with the concept that plasma EPCR originates from both proteolytic and alternative splicing mechanisms. The genomic structure of human EPCR contains four exons, separated by introns. Review of this sequence reveals an in-frame reading sequence after the exon III-intron III boundary (at the 5' GT) that includes a TAA stop codon at position 7527. Since this stop codon is upstream of exon IV that codes for the transmembrane domain, the predicted protein would contain a unique 48 residue carboxyl-terminal tail (coded for by the intron sequence) and would not contain a transmembrane anchor.

Figure 2:
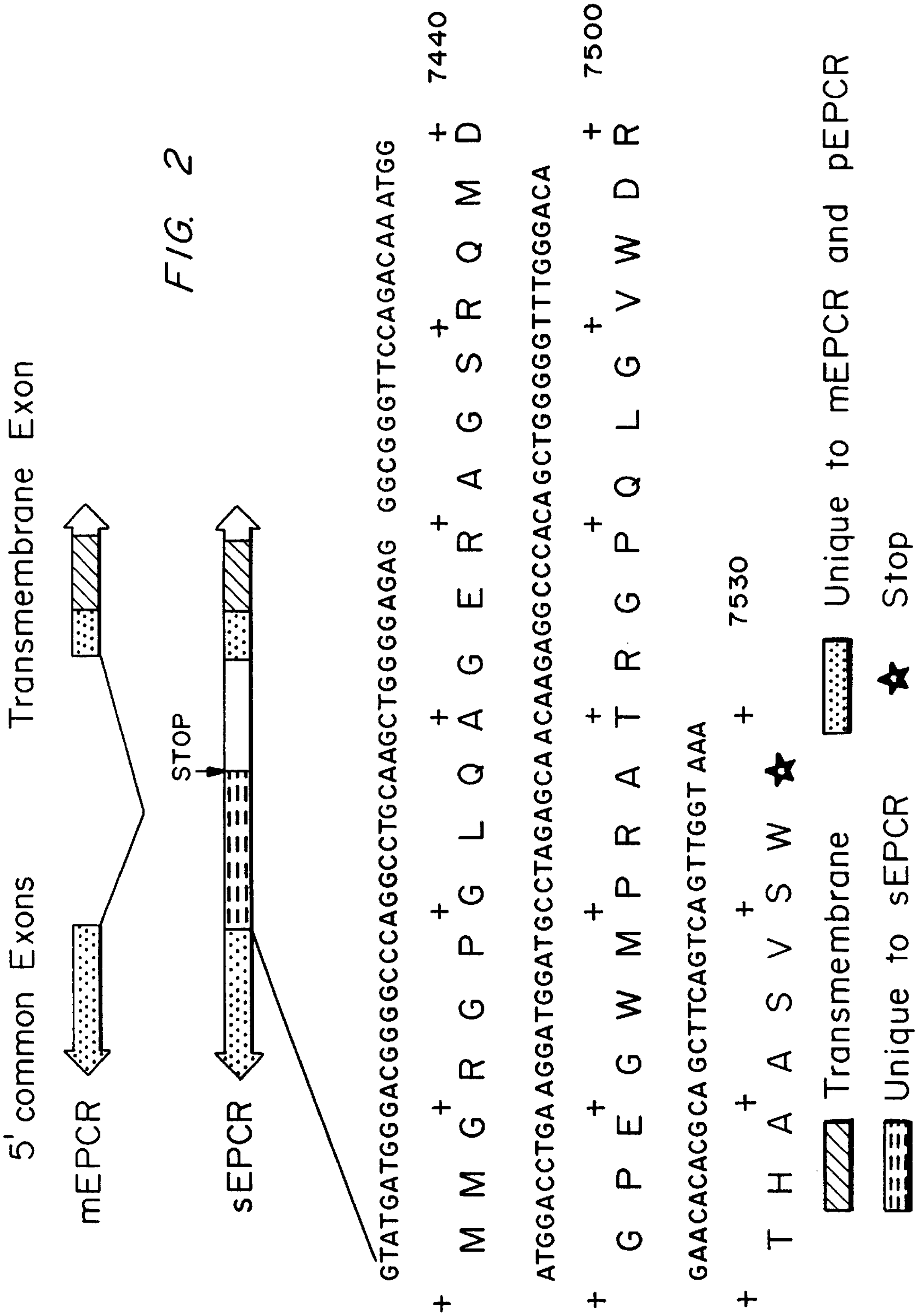
FIG. 2 is a schematic comparing mEPCR and sEPCR, showing the nucleotide insert and encoded amino acid sequence unique to sEPCR.

FIG. 1 is a diagram of two potential ways truncated EPCR can be derived: by proteolysis immediately before the transmembrane domain or by alternative splicing. As shown by FIG. 2, alternative splicing results in inclusion of a peptide sequence in the alternatively spliced truncated EPCR. As shown by FIG. 3, this sequence is highly conserved between species, although slight differences exist, resulting in a new carboxyl-terminal tail of 48 residues for human and bovine EPCR, 51 residues for murine EPCR, and 22 residues for baboon EPCR.

Screening of Patient Samples for Expression of Receptor Proteins.

Patient samples can be screened for the presence of, and amount of, sEPCR or EPCR, using antibodies to either EPCR, the unique insert present in the alternatively spliced insert in EPCR, or antibodies which bind with greater affinity to either EPCR or sEPCR due to conformational differences. Samples can also be screened using other standard techniques to specifically quantitate proteins which are present.

Generation of Antibodies for Diagnostic or Therapeutic Use

Antibodies to EPCR, and in particular, soluble EPCR ("sEPCR"), and recombinant soluble EPCR ("rsEPCR") can be generated which are useful in detection, characterization or isolation of receptor proteins, as well as for modifying receptor protein activity, in most cases, through inhibition of ligand binding. Antibodies are generated by standard techniques, using human or animal purified or recombinant receptor proteins or fragments thereof as the immunogen.

Monoclonal antibodies to EPCR were obtained as described for other proteins by Esmon, et al., 1993. *Methods Enzymol.* 222:359–385. The antibodies referred to as 1494, 1495, and 1496 mAbs are $IgGl_K$ antibodies that bind to recombinant soluble EPCR and to cell surface-expressed EPCR. The 1494 and 1496 mAbs block the binding of protein C and APC to EPCR, and inhibit the ability of cellular EPCR to facilitate protein C activation by the thrombin-thrombomodulin complex. The 1495 mAb does not block ligand binding to EPCR, does not alter cell surface protein C activation, and has a binding epitope distinct from that for 1494 or 1486 mAb. The antibodies can be labelled using standard techniques, such as radiolabelling, enzyme labelling, fluorescent labels such as fluorescein, gold particles, dyes, and other means for detection of the antibodies. For example, antibody can be biotinylated with biotinamidocaproate N-hydroxysuccinimide ester using standard procedures. Antibody can be immobilized to a solid support for use in immunoassays, for example, AffiGel-10™, nitrocellulose, or microtiter wells, or use in solution phase immunoassays.

In a preferred embodiment, EPCR is measured using microtiter plates (Maxisorp™, NUNC NS, Roskilde, Denmark) coated with 50 microliters of 4 micrograms/ml 1495 mAb in 15 mM $Na_2CO_3$, 35 mM $NaHCO_3$, pH 9.6, at 4° C. overnight. At room temperature, the plates are then washed three times with 20 mM Tris-HCl, 0.1M NaCl, 0.05% Tween 20, pH 7.5 (assay buffer), and blocked with assay buffer containing 0.1% (wt/vol) gelatin for at least one hour. The wells are then washed, 50 microliter samples added in triplicate wells, and the plates incubated for one hour. The wells are aspirated, washed three times with assay buffer, and 50 microliters of 2 micrograms/ml biotin-1494 mAb added. The plates are incubated for 1 hour, washed three times, and 50 microliters of 0.25 micrograms/ml streptavidin-alkaline phosphatase conjugate (GIBCO BRL) added and incubated for an additional hour. The wells are washed five times, and the substrate and amplifier reagents from an ELISA amplification kit (GIBCO BRL) added sequentially at 15-min intervals according to the manufacturer's directions. The color development is stopped with 0.3M $H_2SO_4$, and the endpoint absorbance read at 490 nm on a $V_{max}$ microplate reader. Standards in triplicate wells are from 1.5 to 100 ng rsEPCR/ml in 20 mM Tris-HCl, 0.1M NaCl, and 1 mM EDTA, 0.1% gelatin, pH 7.5. The standard curve is linear from 1.5 to 12.5 ng/ml, and samples are diluted with the same buffer to fall within the linear range. Studies show that between one and two percent plasma does not affect the linearity of the assay or the sensitivity of the standard curve. Plasma samples from healthy volunteers were diluted with assay buffer containing 1 mM EDTA to a final 2% plasma, and EPCR antigen levels are calculated from the average of triplicate wells by reference to standard curve determined on the same plate.

Disorders

The assay for soluble EPCR is useful in detection and analysis of coagulation and inflammatory states and disorders as discussed herein, such as autoimmune diseases like lupus, in transplant monitoring, sepsis, shock, pre-eclampsia, diabetes, cardiopulmonary bypass, unstable angina, restenosis, angioplasty (i.e., vascular disease), kidney or liver disease. For example, the EPCR is a marker for large blood vessels, and therefore for damage to large blood vessels. An increase in the amount of soluble EPCR is indicative of large vessel injury, resulting either in proteolysis of EPCR or stimulation of sEPCR synthesis. The ratio of EPCR to thrombomodulin can also be determined, based on either blood or urine samples, which is indicative of the relative extent of microvascular versus large vessel. The relative amounts of EPCR to cytokines, leukocyte activation markers and complement factors or activation markers can also be used to indicate disease state.

Since EPCR is present on endothelial cells, it is useful as a marker of endothelial cell damage. It can be used as an indicator of drug effect, both toxicity as well as efficacy. For example, in lupus patients, drugs effectively minimizing inflammatory/coagulation mediated, large vessel injury would result in decreasing EPCR levels.

The present invention will be further understood by reference to the following non-limiting examples.

EXAMPLE 1

Identification of Functional Endothelial Protein C Receptor in Human Plasma

The following abbreviations are used: rsEPCR, recombinant soluble EPCR with the HPC4 epitope inserted in place of the transmembrane domain and cytosolic tail; mAb, monoclonal antibody; SDS-PAGE, sodium dodecylsulfate polyacrylamide gel electrophoresis.

METHODS

Materials. The following reagents were purchased from the indicated vendors: Porcine intestinal mucosal heparin, diisopropyl fluorophosphate, biotinamidocaproateN-hydroxysuccinimide ester, bovine serum albumin, Sigma (St. Louis, Mo.); Spectrozyme PCa, American Diagnostica (Greenwich, Conn.); ELISA amplification kit, GibcoBRL (Gaithersburg, Md.); AffiGel-10, BioRad (Hercules, Calif.); Hank's balanced salt solution, 3-(N-morpholine)propane sulfonic acid (MOPS), Fisher Scientific (Fair Lawn, N.J.). All other reagents were of the highest quality commercial available.

Proteins. Human protein C (Esmon, et al. 1993. *Methods Enzymol.* 222:359–385), bovine thrombin (Owen, et al. 1974. *J. Biol. Chem.* 249:594–605), and bovine antithrombin (Esmon 1977. "Factors regulating the inhibition of thrombin by antithrombin III. In Chemistry and Biology of Thrombin". R. L. Lundblad, J. W. Fenton, II, and K. G. Mann, editors. Ann Arbor Science, Ann Arbor. 403–411) were purified as described. Recombinant soluble EPCR, rsEPCR, consists of the extracellular domain of EPCR truncated at residue 210 just before the transmembrane domain, followed by a 12 residue sequence that permits calcium-dependent immunoaffinity purification on the HPC4 monoclonal antibody (Takahashi, et al. 1992; Stearns, et al. 1988. *J. Biol. Chem.* 263:826–832). The construction, purification, and protein C/APC binding characteristics of rsEPCR (Fukudome, et al. 1996). Goat preimmune serum and polyclonal antiserum to rsEPCR was prepared and the IgG purified (Fukudome, et al. 1996). Goat anti-rsEPCR polyclonal antibody was biotinylated with biotinamidocaproate N-hydroxysuccinimide ester using standard procedures.

Monoclonal antibodies. Monoclonal antibodies (mAb) against rsEPCR were obtained as described for other proteins (Esmon, et al. 1993). The 1494, 1495, and 1496 mAb are IgG1k antibodies that bind to rsEPCR and to cell surface-expressed EPCR. The 1494 and 1496 mAb block the binding of protein C and APC to EPCR and inhibit the ability of cellular EPCR to facilitate protein C activation by the thrombin-thrombomodulin complex (Stearns-Kurosawa, et al. 1996). The 1495 mAb does not block ligand binding to EPCR, does not alter cell surface protein C activation and has a binding epitope distinct from that for 1494 or 1496 mAb. The 1494 and 1495 mAbs were biotinylated with biotinamidocaproate N-hydroxysuccinimide ester using standard procedures. The 1494 mAb was coupled to AffiGel-10, according to the manufacturer's directions, for immunoaffinity purification of plasma EPCR. The screening of anti-EPCR mAb was done using methods described by Stearns-Kurosawa, et al. (1996); Fukudome, et al. (1996).

Clotting Assay. The effect of rsEPCR or purified plasma EPCR on APC (25 nM) anticoagulant activity in a one-stage factor Xa clotting assay was performed (Regan, et al. 1996) in the presence or absence of 83 $\mu$g/ml 1496 mAb, an antibody that blocks APC-EPCR interaction (Stearns-Kurosawa, et al. 1996). The soluble EPCRs and 1496 mAb were pre-incubated for 15 minutes before assay.

Cell Culture. All human cell lines were maintained as described previously (Fukudome, et al. 1996). EA.hy926 cells, a transformed human endothelial cell line (Edgell, et al. 1983. *Proc. Natl. Acad. Sci.* (*USA*) 80:3734–3737), were kindly provided by Cora-Jean Edgell (University of North Carolina at Chapel Hill).

Flow Cytometric Analysis. To serve as a fluorescent probe, APC was labeled with fluorescein in the active site (fl-APC) as described (Fukudome and Esmon, 1994; Bock, P. E. 1988. *Biochemistry* 27:6633–6639). The effect of rsEPCR or plasma EPCR on APC binding to EA.hy926 cells was studied by flow cytometry (Fukudome, et al. 1996). Briefly, harvested cells were incubated for 30 min on ice with 60 nM fl-APC in the absence or presence of increasing concentrations of either soluble EPCR preparation, washed, and cell-bound fluorescence was determined by flow cytometry with 10,000 events counted per sample. All assays were done in Hank's balanced salt solution supplemented with 1% bovine serum albumin, 3 mM $CaCl_2$, 0.6 mM $MgCl_2$, and 0.02% sodium azide.

Cell surface protein C activation. EA.hy926 cells were cultured in 96-well tissue culture dishes (Stearns-Kurosawa, et al. 1996). The confluent monolayers were washed three times with Hank's balanced salt solution supplemented with 1% (w/v) bovine serum albumin, 3 mM $CaCl_2$, 0.6 mM $MgCl_2$, and 0.02% sodium azide. All assays were done at room temperature in the same buffer in 60 $\mu$l final volume, and all protein concentrations represent the final concentration in the assay. Protein C was added (0.1 $\mu$M) in the absence or presence of rsEPCR, plasma EPCR, or 1494 mAb at the indicated concentrations and pre-incubated with the cells for 15 minutes. Thrombin was added to the mixtures (2 nM) to start the activation reactions. At the indicated time, 50 $\mu$l aliquots were removed and added to 10 $\mu$l of antithrombin (0.7 $\mu$M final) and heparin (5 U/ml final) in a 96-well microtiter plate. APC amidolytic activity was determined by addition of Spectrozyme PCa substrate (0.2 mM) and the rate of change in absorbance at 405 nm (mOD/min) was measured on a Vmax kinetic microplate reader (Molecular Devices, Menlo Park, Calif.). All assay points were done in triplicate wells and less than 10% of the protein C substrate was activated as determined by reference to a standard curve of fully activated protein C versus mOD/min.

Plasma and Serum Collection. Whole blood was collected from normal adult volunteers (12 females and 10 males) by venipuncture into 3.8% buffered citrate solution or into tubes without anticoagulant (Vacutainer tubes; Becton Dickinson, Franklin Lakes, N.J.). No screening of donors was attempted with respect to age, diet or other variables. All volunteers were informed of the study and gave their written consent. The blood was centrifuged at 1160×g for 10 min. The plasma and serum were aliquoted and stored frozen at –80° C. until assay.

ELISA for quantitation of plasma EPCR. An enzyme-linked immunosorbent assay for detection of EPCR antigen in plasma was developed. Microtitre plates (Maxisorp; Nunc, Roskilde, Denmark) were coated with 50 $\mu$l of 4 $\mu$g/ml 1495 mAb in 15 mM $Na_2CO_3$, 35 mM $NaHCO_3$, pH 9.6 at 4° C. overnight. The following steps were done at room temperature. The wells were washed three times with 20 mM Tris-HCl, 0.1M NaCl, 0.05% Tween 20, pH 7.5 (assay buffer) and blocked with assay buffer containing 0.1% (w/v) gelatin for at least one hour. The wells were washed, 50 $\mu$l samples were added in triplicate wells, and the plates were incubated for one hour. The wells were aspirated, washed three times with assay buffer and 50 $\mu$l of 2 $\mu$g/ml biotin-1494 mAb was added. The plates were incubated for one hour, washed three times and 50 $\mu$l of 0.25 $\mu$g/ml streptavidin-alkaline phosphatase conjugate (GibcoBRL) was added and incubated for an additional one hour. The wells were washed five times and the substrate and amplifier reagents from an ELISA amplification kit (GibcoBRL) were added sequentially at 15 minute intervals according to the manufacturer's directions. The color development was stopped with 0.3M $H_2SO_4$ and the endpoint absorbance at 490 nm was read on a Vmax microplate reader. Each plate contained standards in triplicate wells from 1.5–100 ng/ml rsEPCR in 20 mM Tris-HCl, 0.1M NaCl, 1 mM EDTA, 0.1% gelatin, pH 7.5. The standard curve was linear (r=0.99) from 1.5–12.5 ng/ml and plasma samples were diluted with the same buffer to fall within the linear range. Preliminary experiments determined that a final concentration of 1–2% human plasma did not affect the linearity or sensitivity of the standard curve. Plasma samples from healthy volunteers were diluted with assay buffer containing 1 mM EDTA to a final 2% plasma and EPCR L, antigen levels were calculated from the average of triplicate wells by reference to a standard curve determined on the same plate.

An alternative assay was developed in which the coating and detecting antibodies were reversed (1494 mAb coating; biotin-1495 mAb detecting) and antibody binding was detected with the Blue Phos substrate (KPL Laboratories; Gaithersburg, Md.). this method was used to assay plasma EPCR in the sepsis patients. This assay was more sensitive, probably because of affinity differences, but both assays gave qualitatively similar results.

Western Blot. Sodium dodecyl sulfate polyacrylamide gel electrophoresis (SDS-PAGE) of plasma or serum samples was done with 10% acrylamide gels with the Laemmli buffer system (*Nature* 227:680–685) under non-reducing conditions using standard procedures. Gels were transferred to polyvinylidine membranes (PVDF; Millipore, Bedford, Mass.), the membranes blocked, and then incubated for 30 minutes with either pre-immune goat IgG (50 μg/ml) or a goat anti-rsEPCR polyclonal IgG (50 μg/ml). After washing, membranes were incubated with mouse anti-goat IgG-horseradish peroxidase conjugate (Pierce, Rockford, Ill.) at a 1:20,000 dilution for 30 minutes. Membranes were washed and bound antibody-enzyme conjugate was detected with an enhanced chemiluminescent substrate (Pierce) according to the manufacturer's instructions.

Immunoadsorption. Serum or citrated plasma samples (400 μl) from healthy volunteers were incubated with 50 μl of 1495 mAb conjugated to AffiGel-10 (5 mg IgG/ml resin) overnight at 4° C. with mixing. The samples were centrifuged, the supernatant was removed, and the resin was washed three times with 1 ml of 20 mM Tris-HCl, 0.1M NaCl, 0.02% sodium azide, pH 7.5. SDS-PAGE sample buffer containing a final 20 mM dithiothreitol was added to the washed resin, the samples were boiled for three minutes, and processed for SDS-PAGE and Western blotting. Membranes were probed with biotinylated-goat anti-rsEPCR polyclonal antibody at 4 μg/ml and bound antibody was detected with a streptavidin-horseradish peroxidase conjugate (Pierce) and enhanced chemiluminescent detection system. Preliminary experiments determined that pre-adsorption of samples with 100 μl of Tris-inactivated AffiGel-10 resin for 1–4 hours at room temperature, followed by overnight immunoadsorption with the 1495 mAb-AffiGel-10 gave identical Western blotting results.

Purification of plasma EPCR. Plasma EPCR as purified from human citrated plasma (Oklahoma Blood Institute) using a combination of ion-exchange chromatography, anti-rsEPCR mAb immunoaffinity chromatography, and chromatography on protein C affinity columns. Two preparations were done in slightly different ways.

In the first preparation, plasma (1L) was diluted with an equal volume of 20 mM Tris-HCl, pH 7.5, 10 mM benzamidine, 400 units sodium heparin and batch-adsorbed for 1 hour with 1 g pre-swollen QAE resin. After settling, the resin was processed for purification of protein C (Esmon, et al. 1993). Solid ammonium sulfate was added to the supernatant at 4° C. to 40% saturation, centrifuged, and additional ammonium sulfate was added to that supernatant to achieve 70% saturation. After centrifugation, the soft pellet was placed in dialysis bags and dialyzed overnight against 12 L of 20 mM Tris-HCl, 0.02% sodium azide, pH 7.4. The dialysate was applied to a 1496 mAb-AffiGel-10 immunoaffinity column (6 ml resin; 5 mg IgG/ml resin) equilibrated in 20 mM Tris-HCl, 0.1M NaCl, 0.02% sodium azide, pH 7.4. The column was washed with more than 12 ml of the same buffer and eluted with 50% (v/v) ethylene glycol in 20 mM Tris-HCl, pH 7.4 (Jun Xu, unpublished observations). The peak fractions from the elution were pooled (0.37 total $OD_{280}$), concentrated (Centriprep 30, Millipore), and the buffer exchanged to 20 mM Tris-HC1, 0.1M NaCl, 3 mM $CaCl_2$, 0.6 mM $MgCl_2$, 0.02% sodium azide, pH 7.4. This material was applied to a protein C affinity column that had been previously prepared by applying the purified protein C (3 mg) to an HPC4-AffiGel-10 column (5 mg IgG/ml resin; 0.9×8 cm) in the same buffer. The HPC4 mAb binds the protein C activation region in a calcium-dependent fashion (Esmon, et al. 1993; Stearns, et al. 1988) and does not interfere with subsequent binding of EPCR to protein C. After applying the sample containing plasma EPCR, the column was washed with approximately 12 ml of buffer and eluted with 20 mM Tris-HCl, 0.1M NaCl 5 mM EDTA, 10 mM MOPS, 0.02% sodium azide, pH 7.5. Fractions were monitored for absorbance at 280 nm and for EPCR antigen using the ELISA described above. The eluate containing both protein C and plasma EPCR was applied to an FPLC (Pharmacia-LKB, Uppsala, Sweden) Mono Q column and the column developed with a linear gradient of 0.1–1M NaCl in 20 mM Tris-HCl , pH 7.5. About half of the plasma EPCR did not bind to the Mono Q column, half eluted at about 0.2M NaCl, and the protein C eluted at approximately 0.5M NaCl. Both ionic species of plasma EPCR appeared identical on SDS-PAGE gels under reducing or non-reducing conditions with silver staining, with Coomassie BB staining or with gold staining (Pierce) after transfer to PVDF membranes, and on Western blots with the biotin-polyclonal anti-rsEPCR antibody probe.

The second preparation of plasma EPCR was done starting with 4L of plasma to purify enough protein for functional studies. In this case, the 1496-AffiGel-10 resin (20 ml of 5 mg IgG/ml resin) was added directly to the citrated plasma, along with final concentrations of 10 mM benzamidine, 1 mM diisopropylfluorophosphate, and 0.5 units/ml sodium heparin. The plasma was batch-adsorbed overnight at 4° C. with gentle mixing. After the resin settled, the supernatant was processed for protein C purification (Esmon, et al. 1993). The resin was packed into a 2.5×30 cm column, washed extensively with 20 mM Tris-HCl, 0.1M NaCl, 0.02% sodium azide, pH 74 and eluted with 50% ethylene glycol in 20 mM Tris-HC1, pH 7.4. The eluate was pooled and concentrated (5.5 total $OD_{280}$), applied to a Mono Q column and the two ionic species (breakthrough and 0.2M NaCl eluate peak) were re-applied to the 1496-AffiGel-10 resin (1.5×11 cm). The column was eluted with 50% ethylene glycol as before. The eluate (0.71 ODs) was concentrated and the buffer exchanged to 20 mM Tris-HCl, 0.1M NaCl, 3 mM $CaCl_2$, 0.6 mM $MgCl_2$, 0.02% sodium azide with a Centriprep 30. This material was then applied to an affinity column in which protein C (2.9 mg) had been initially applied in the same buffer to an HPC2-AffiGel-10 column (0.6×17 cm). The HPC2 mAb binds to the protein C serine protease domain and does not interfere with EPCR binding (Fukudome, et al. 1996). The bound EPCR was eluted with buffer containing 5 mM EDTA. Contaminating serum amyloid P (from the protein C sample) was removed by ion-exchange chromatography on the FPLC Mono Q column. The sample was applied in 0.2M NaCl, so that the plasma EPCR did not bind, and was separated from the contaminants which eluted at 0.4–0.5M NaCl. The resultant purified plasma EPCR (0.193 $OD_{280}$) appeared homogenous by SDS-PAGE with silver staining and by Western blotting with polyclonal anti-rsEPCR. This material was used for the functional studies and amino-terminal sequence analysis.

Protein Sequencing. The amino-terminal sequence analysis of soluble plasma EPCR was performed in Dr. Kenneth Jackson's laboratory at the Molecular Biology Research Facility, W. K. Warren Medical Research Institute, Oklahoma City. Amino acids are designated by the standard one letter code.

RESULTS

As a first approach, plasma and serum samples from three healthy volunteers were diluted (4% v/v), run on 10% SDS-PAGE gels under non-reducing conditions, and processed for Western blotting using a goat polyclonal antibody raised against rsEPCR. Plasma and serum samples (4% v/v) from healthy volunteers were processed for SDS-PAGE on 10% gels under non-reducing conditions, transferred to membranes and the membranes probed with goat anti-rsEPCR polyclonal antibody. Results were compared to rsEPCR (0.2 ng). Bound antibody was detected with mouse anti-goat IgG and an enhanced chemiluminescence detection system. Plasma samples from two healthy volunteers were immunoadsorbed with 1495 AffiGel-10 resin. The washed resin was eluted and processed for SDS-PAGE under reducing conditions. Western blotting was done using biotin-goat anti-rsEPCR as a probe.

Plasma EPCR purity was determined from silver stained SDS-PAGE 10% gels and western blots of membranes probed with biotin-goat anti-rsEPCR (reduced and non-reduced). A single band of approximately 43,000 Da appears in both the serum and plasma samples after the membrane is probed with the polyclonal antibody. The size of the protein detected appears slightly larger than the rsEPCR. The other bands detected were background binding of IgG as judged by probing with preimmune IgG and longer exposure times. overnight incubation of plasma samples with the anti-EPCR 1495 mAb coupled to AffiGel-10 resin, followed by washing and elution of bound antigen under reducing conditions, resulted in a single band detected by Western blotting with biotin-goat anti-rsEPCR polyclonal antibody.

Determination of soluble EPCR antigen in plasma from healthy volunteers by ELISA using mAb 1495 as the coating antibody found antigen levels of 91.1 +/− 24.5 ng/ml in females (n=12) and 107.2 +/− 30.2 ng/ml in males (n=10). When calculated together, the average plasma EPCR antigen level was 98.4 +/− 27.8 ng/ml. The value for males appeared to be slightly higher than for females, similar to thrombomodulin (Quehenberger, et al. *Thromb. Haemost.* 76: 729–734), although the population studied was too limited for statistical analysis and this study was not designed to assess differences due to gender, age, diet or other variables.

Since the plasma EPCR appeared to be a single species at approximately 100 ng/ml, it became important to determine whether the circulating EPCR could bind protein C and APC. Soluble EPCR was purified from human plasma by a combination of ion-exchange chromatography, precipitation with ammonium sulfate, and immunoadsorption by anti-EPCR 1496 mAb-AffiGel-10 column chromatography as described in Experimental Procedures.

This plasma EPCR (approximately 110 μg) was applied to a protein C affinity column prepared by applying protein C (3 mg) to an anti-protein C HPC4 mAb-AffiGel-10 column in buffer containing 3 mM $CaCl_2$, 0.6 mM $MgCl_2$ The column was washed and plasma EPCR was applied at fraction 19. The column was washed and eluted with buffer containing 5 mM EDTA starting at fraction 35. Absorbance at 280 nm and EPCR antigen was determined for the fractions. EPCR antigen was determined by ELISA.

More than 98% of the applied plasma EPCR antigen bound to the protein C affinity column. The absorbance profile indicates co-elution of EPCR and protein C from the antibody column, consistent with the calcium-dependence of protein C binding to this antibody (Stearns, et al. 1988).

To purify sufficient protein for functional and structural studies, EPCR was purified from 4L of plasma using a similar, but slightly modified procedure. After elution from a protein C-antibody affinity column, residual contaminating proteins were removed by ion-exchange chromatography on an FPLC Mono Q column. The resultant preparation of plasma EPCR appeared homogenous on SDS-PAGE 10% gels with silver staining and identical results were obtained with western blots probed with biotin-goat anti-rsEPCR polyclonal antibody under both reducing and non-reducing conditions. Amino-terminal sequence analysis of the purified protein yielded only one sequence, S-Q-D-A-S-D, which is identical to the amino-terminal sequence of recombinant soluble EPCR (Sequence ID No. 2). This is the first amino-terminal sequence determination of EPCR from a natural source.

Figure 4A:
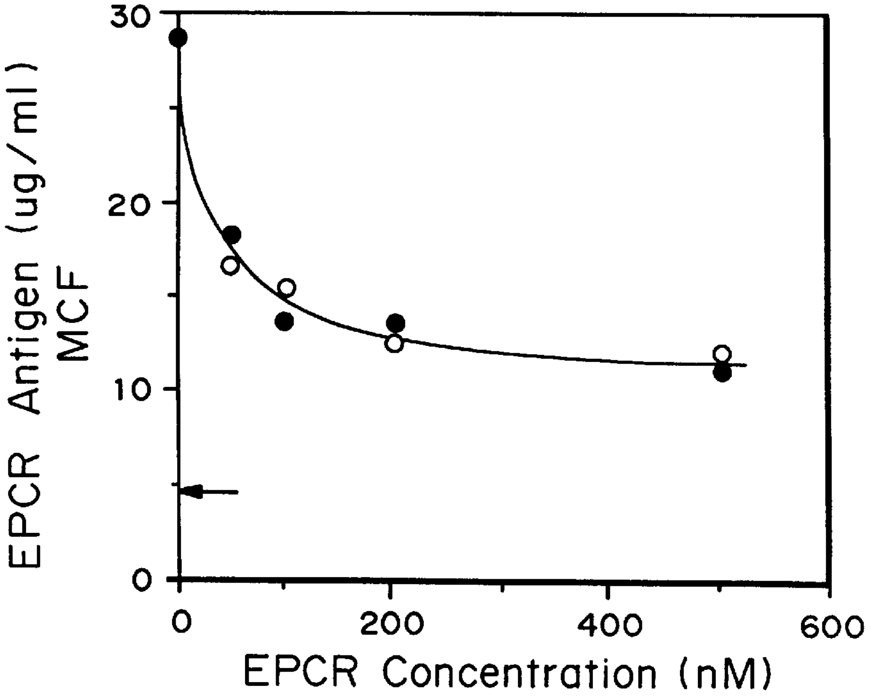
FIG. 4*a* is a graph showing that soluble plasma EPCR binds to human protein C and APC. EA.hy926 cells were incubated with 60 nM fl-APC in the presence of 0–500 nM rsEPCR (●) or plasma EPCR (○) for 30 minutes on ice. The cells were washed and cell-bound fluorescence was determined by flow cytometry as described. The intrinsic cell fluorescence in the absence of added fl-APC is indicated by the arrow. The mean cell fluorescence (MCF) plotted represents the average of duplicate MCF determinations.

The ability of plasma EPCR to bind to APC was assessed by competition studies in which plasma EPCR was allowed to compete with cellular EPCR for APC, and the resultant free APC that could bind to cellular EPCR was assessed by flow cytometry (FIG. 4*a*). APC labeled with fluorescein in the active site (fl-APC) was incubated with EA.hy926 cells in the presence or absence of either plasma EPCR or rsEPCR. The EPCR concentration dependence for inhibition of APC binding to the cells was similar for both soluble forms of EPCR. This observation indicates that the affinity of plasma EPCR for binding APC is similar to that previously determined for the rsEPCR-APC binding interaction ($Kd_{app}$approximately 30 nM).

Figure 4B:
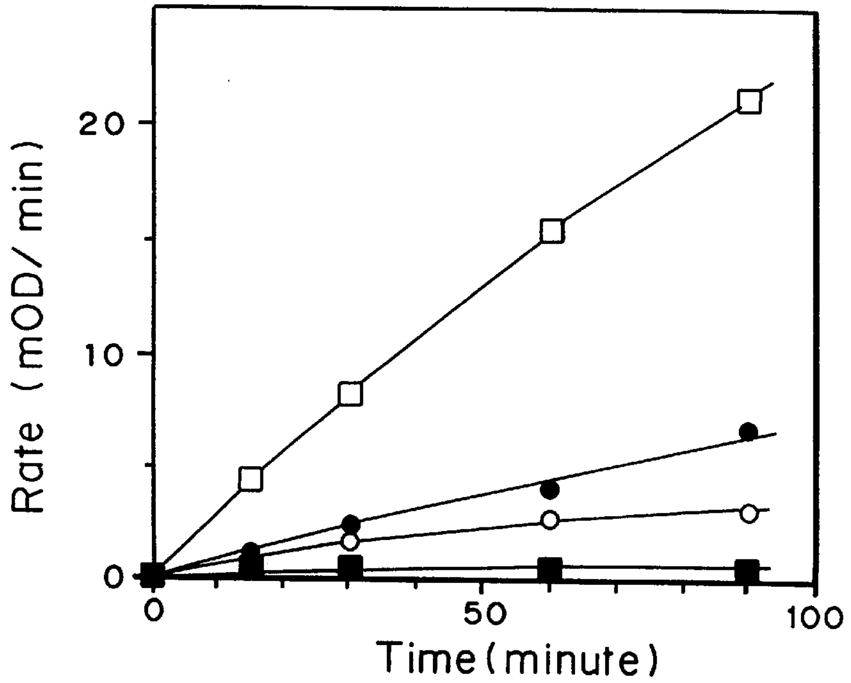
FIGS. 4*b* and 4*c* are graphs showing soluble plasma EPCR and rsEPCR inhibit protein C activation on cell surfaces.
Figure 4C:
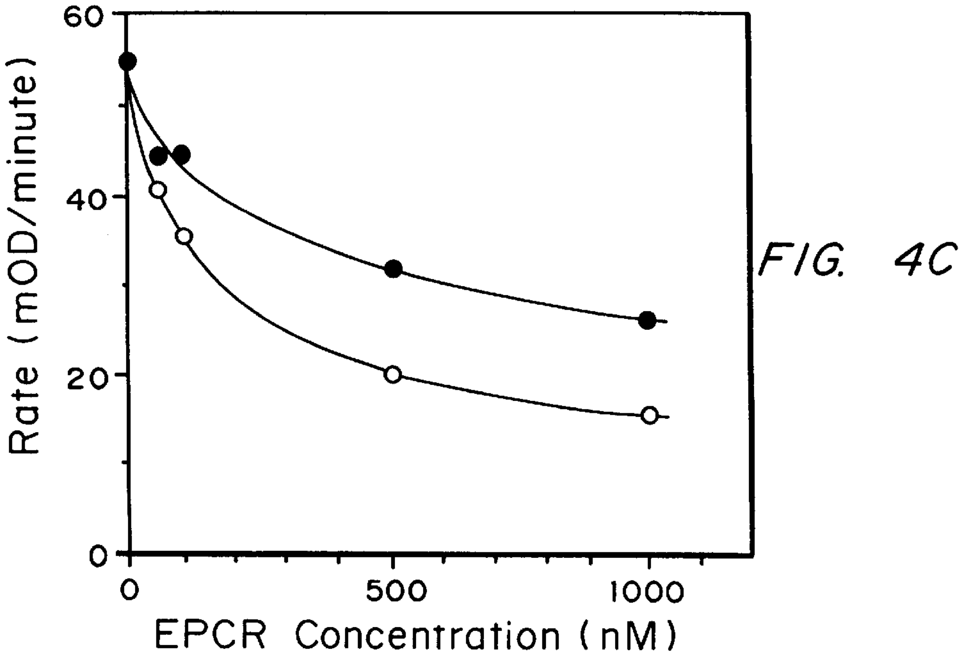

While rsEPCR has little effect on protein C activation in a soluble system (Regan, et al. 1996), membrane-bound EPCR has a very potent ability to facilitate activation on cell surfaces (Stearns-Kurosawa, et al. 1996). The current data demonstrating the existence of a circulating form of EPCR capable of binding protein C and APC suggested that plasma EPCR has the potential to alter cell-surface activation of protein C. The thrombin-dependent activation of an approximately physiological level of protein C (0.1 μM) on EA.hy926 cells was inhibited by excess rsEPCR almost to the level of that observed with the anti-rsEPCR 1494 mAb that blocks the EPCR-protein C binding interaction, as shown by FIG. 4*b*. Previous studies have demonstrated that rsEPCR has no effect on APC amidolytic activity using small synthetic substrates (Regan, et al. 1996). The plasma EPCR was slightly more effective in its ability to inhibit cell-surface protein C activation on the EA.hy926 cells relative to the rsEPCR, as shown by FIG. 4*c*.

Figure 4D:
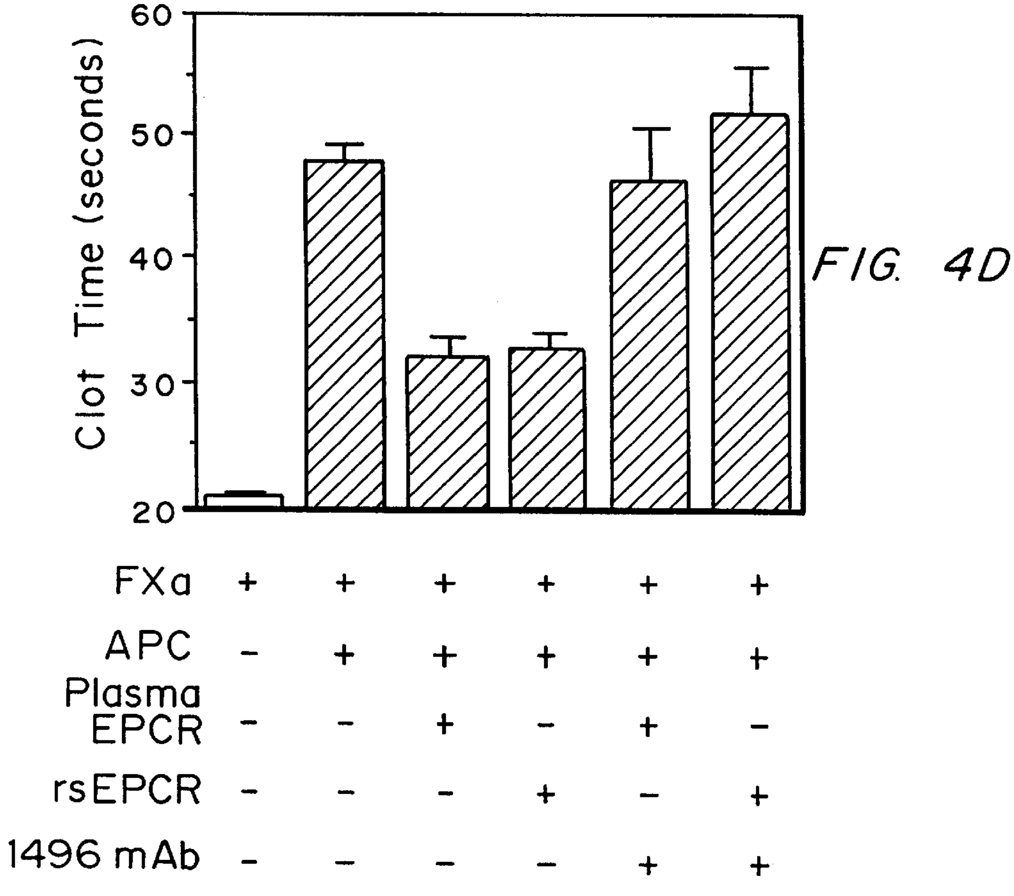
FIG. 4*d* is a graph showing soluble plasma EPCR inhibits APC anticoagulant activity The anticoagulant activity of APC (25 nM) was determined with a one-stage Xa clotting assay in the presence of 460 nM plasma EPCR or rsEPCR. The effect was reversed when either soluble EPCR was pre-incubated for 5 minutes with 42 μg/ml of 1496 mAb which blocks binding of APC to EPCR. The data represent the average of 4–6 determinations±S.D.

In a one-stage factor Xa clotting assay, purified plasma and soluble recombinant EPCR inhibited the APC prolongation of clotting times similarly (FIG. 4*d*). Inhibition of APC anticoagulant activity by rsEPCR had been observed previously (Regan, et al. 1996). As expected, the 1496 mAb reversed this effect by blocking the APC-plasma EPCR binding interaction.

EXAMPLE 2

Detection of Soluble EPCR in Urine.

To address the question of whether soluble EPCR is present in urine, four urine samples were collected (first morning void) and analyzed for the presence of soluble EPCR by western blotting and ELISA.

Undiluted pediatric urine samples were compared to a 4% normal plasma and recombinant soluble EPCR (1 ng). The samples were incubated with biotin-goat-anti-rsEPCR and a streptavidin-alkaline phosphatase detection system.

The western blot indicates that a) soluble EPCR is present in urine, and b) the soluble EPCR antigen is present at a size similar to that observed in plasma. Obvious degradation is not observed. The amount of soluble EPCR in the four samples as quantified by ELISA was 40.3, 6.1, 35.6, and 90.1 ng/ml.

EXAMPLE 3

Measurement of Plasma EPCR from Lupus Patients.

Normal human plasma EPCR concentration are about 100 ng/ml (98.4±27.8 ng/ml; 2.5 nM), as discussed above. A panel of samples from patients with lupus erythematosus (n=54) was assayed and soluble EPCR levels were found to range from non-detectable levels to greater than 1,700 ng/ml. Fifteen patients had soluble EPCR levels greater than 200 ng/ml.

Figure 5:
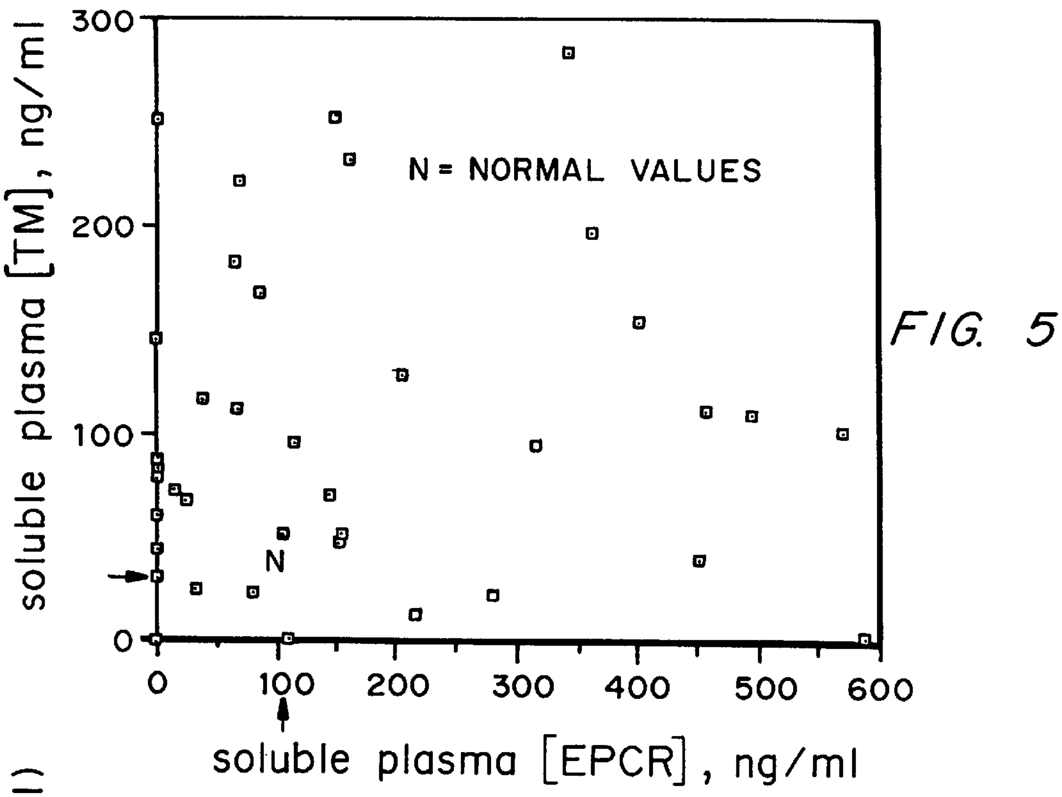
FIG. 5 is a graph comparing levels of soluble plasma TM to soluble plasma PCR in lupus patients, demonstrating that there is no correlation between TM and EPCR values, but that the majority of lupus patients exhibit extremely elevated levels of soluble plasma EPCR.

Previous studies have shown elevated soluble plasma TM levels in lupus patients due to endothelial damage and the current lupus patient samples were assayed for plasma TM as a reference. It was found that their soluble TM levels had absolutely no correlation with their soluble EPCR levels, as shown by FIG. 5. This is an important observation that suggests that the source of the soluble plasma EPCR is not simply from randomly damaged endothelium. In contrast to TM, membrane-bound EPCR expression in humans and primates is restricted primarily to the endothelium of large vessels, with capillaries expressing little EPCR. The distinctive localization of EPCR is expected to augment protein C activation locally to prevent large vessel thrombosis. The primary localization of membrane-bound EPCR to the large vessels points to a targeted thrombotic risk in the large vessels that may be predicted by soluble plasma EPCR concentrations.

EXAMPLE 4

Plasma Soluble EPCR in Septic Shock Patients.

Sepsis (accp/sccm consensus conference, chest 1992; 101:1644–1655) is defined as the systemic inflammatory response to infection, including, but not limited to, more than one of the following clinical manifestations:

1) body temperature greater than 38° C. or less than 36°C.;
2) heart rate greater than 90 beats per minute;
3) tachypnea manifested by:
   a) respiratory rate greater than 20 breaths per minute;
   b) hyperventilation as from $PaCO_2$ of less than 32 mm Hg;
4) WBC count greater than 12,000/$mm^3$ or less than 4,000/$mm^3$, or presence of more than 10% immature neutrophils (bands).

Samples were obtained from patients with post-surgical complications with or without severe sepsis, as defined by sepsis associated with organ dysfunction, hypoperfusion or hypotension. Perfusion abnormalities may include lactic acidosis, oliguria, or acute alterations in mental status. Septic shock refers to sepsis with hypotension requiring vasoactive drugs for more than 24 hours in spite of adequate fluid resuscitation and the absence of cardiogenic shock.

All the patients included in the study fullfilled the following criteria:

a) admission to the intensive care unit because of sepsis and/or post surgical complications requiring respiratory (controlled ventilation for more than 24 hours) and or hemodynamic support (requirement of inotropic drugs, dopamine or dobutamine at greater than or equal to 5 micrograms/Kg/min and/or vasoactive amines, epinephrine or nor-epinephrin);
b) age between 18 and 75 years;
c) antithrombin activity less than 70% (tested locally). Patients were excluded if they had polytrauma, liver cirrhosis or acute liver failure, cancer in terminal phase, immunodeficiency, leukemia, pregnancy, or heparin therapy.

Patient blood samples were taken at time 0 (entry into the Intensive Care Unit, ICU) and at two days and six days after treatment with anti-thrombin II (ATIII) or a placebo. Plasma soluble EPCR and soluble thrombomodulin (TM) were assayed only on time 0 samples.

sEPCR:
normal: 133.4±53.4 ng/ml (mean±SD)
sepsis: 224.9±74.5 ng/ml
Significant difference between the means, P=0.00009
sTM:
normal: 35.5±20.4 ng/ml (mean±SD)
sepsis: 39.9±73.1 ng/ml
No significant difference between the means, P=0.81 No correlation between sEPCR and sTM levels in plasma, $r^2$=0.34.

Figure 6:
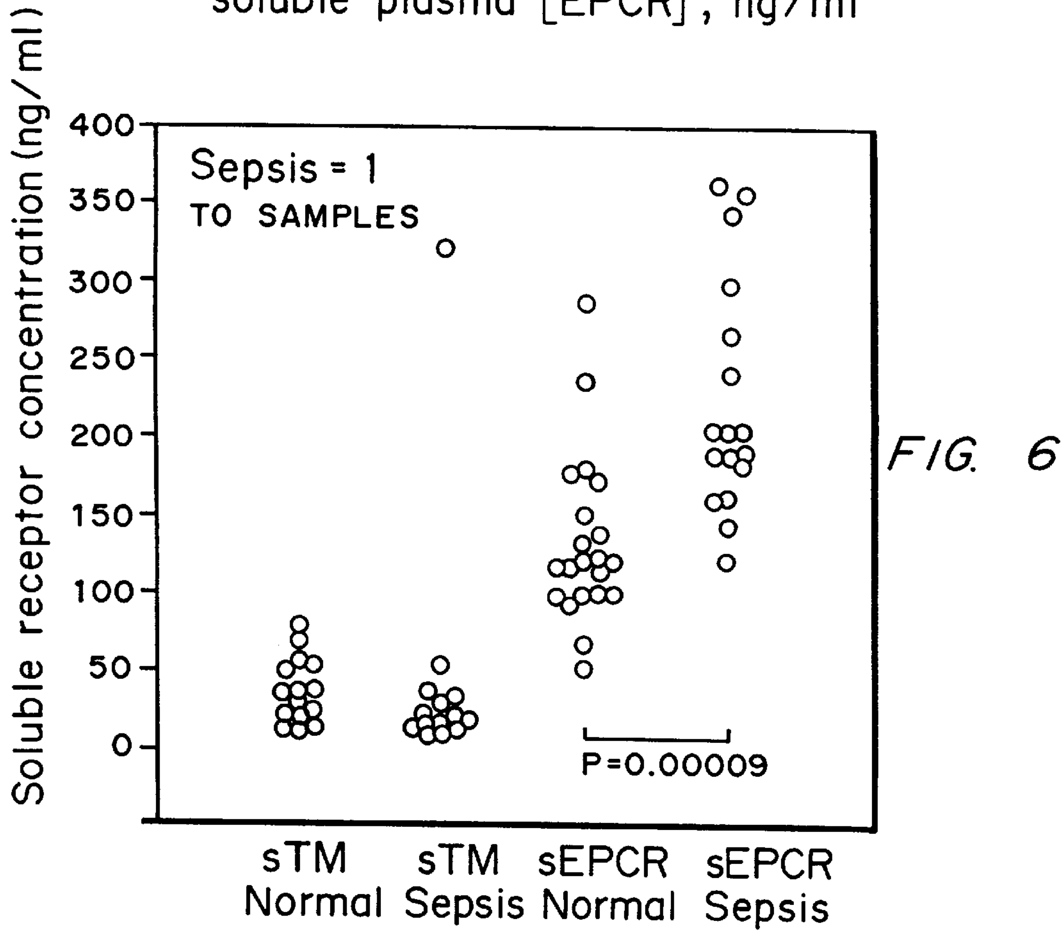
FIG. 6 is a graph of soluble receptor concentration (ng/ml) for sTM (normal), sTM (sepsis), sEPCR (normal), and sEPCR (sepsis). No correlation between sTM and sEPCR, $V^2$=0.034.

These results are shown graphically in FIG. 6. As in the lupus patients, patients with sepsis show very significant elevations in plasma EPCR levels, not correlated with soluble TM levels.

The observation that soluble plasma EPCR inhibits both protein C activation and activated protein C anticoagulant activity indicates that the elevated plasma EPCR levels in these patients poses an additional thrombotic risk and marks evidence of vascular injury/responsiveness. Examples of conditions these are indicative of include disorders associated with endothelial cell stimulation, atherogenesis, leukocyte adhesion and plaque rupture.

EXAMPLE 5

Identification of Alternatively Spliced forms of EPCR in Baboon and Human Tissues.

As an initial approach to determine whether a soluble EPCR isoform could be generated by alternative splicing mechanism, RNA was isolated from human and baboon tissues and reverse transcriptase-PCR (RT-PCR) performed with gene-specific primers. Although the baboon EPCR genomic sequence is not known, primers based on the human sequence were used based on the reasoning that baboons and humans are closely related on the evolutionary scale.

In the RT-PCR procedure generally, total RNA is isolated from homogenized tissue. The RNA is mixed with a specific antisense primer, nucleotides and the reverse transcriptase enzyme. In the mix, the RNA serves as a template for the reverse transcriptase to create a first strand cDNA. This new cDNA template is then amplified by conventional PCR using specific primers and Taq polymerase. Primers that would amplify both the membrane form of EPCR (424 bp) and the predicted alternatively spliced product (674 bp) were chosen. Products corresponding to both forms of EPCR were amplified from a variety of baboon tissues (FIG. 4) and human lung and placenta. Possible contamination with genomic DNA was unlikely as judged by controls without reverse transcriptase and the lack of a 1,885 bp band in the reactions with the tissues.

To confirm that the baboon genomic DNA sequence has the appropriate exon-intron boundary and the intron-inframe reading sequence for alternative splicing, the intron sequence from baboon kidney genomic DNA was amplified by conventional PCR. The assumption was made that the genomic structure was retained between the species and primers were used (human sequence) that flank intron III. This is the intron (human sequence) believed to contain the alternatively spliced sequence. Baboon kidney tissue was homogenized and the DNA extracted. The DNA was mixed with the specific primers and a product amplified by PCR. The DNA product was purified and electrophoresed on an agarose gel.

Procedural Details

A. EPCR ELISA: The coating antibody is 1494 mAb that binds to the ligand binding domain of EPCR. The detecting antibody is biotinylated 1495 mAb, which does not block protein C/APC binding, and does not cross-react with 1494 mAb. The detection system is streptavidin-alkaline phosphatase and BluePhos substrate (from KPL).

B. RT-PCR of tissues: Tissues (50–100 mg) were homogenized in Trizol (Gibco BRL). The upper phase containing RNA was extracted with chloroform, precipitated with isopropanol, washed and solubilized in DEPC-water. RNA (1–5 $\mu$g) was mixed with nucleotides, the CREA antisense primer, and reverse transcriptase in the appropriate buffer according to the manufacturer's directions (Superscript™ Preamplification system for first strand cDNA synthesis, Gibco BRL). The cDNA product was amplified by conventional PCR using the CRES and CREA primers for 30 cycles. The cDNA products were purified by chloroform extraction and alcohol precipitation, solubilized in water and electrophoresed in a 2% agarose gel using standard procedures. Gels were stained with Vistra Green (Amersham) and imaged on a phosphoimager (Storm™ scanner, Molecular Dynamics, Inc.).

C. PCR of baboon genomic DNA: Baboon kidney DNA (82 mg) was homogenized in Trizol reagent. The lower phase containing DNA was extracted, precipitated and solubilized in sterile water. The DNA was amplified by conventional PCR in a mix with buffer, nucleotides, and the HRT-1 and HRT-2 primers for 30 cycles. The amplified DNA was extracted, precipitated, solubilized in sterile water and electrophoresed on a 2% agarose gel using standard procedures. The single band (465 bp) was visualized with ethidium bromide, cut out and the PCR product purified on a spin column according to the manufacturer's directions (Qiagen). The PCR product was sequenced using the same primers.

D. Primer Sequences:

CRES: 5'-TCGTGCGCCTGGTGCACCAGGAGC-3' (5' sense primer near end of exon II)

CREA: 5'-CGCCGTCCACCTGTGCACAGGAAG-3' (3' antisense primer within exon IV)

HRT-1: 5'-AGCAGCTCAATGCCTACAACCG-3' (5' sense primer near end of exon III)

HRT-2: 5'-CCGTAGAAGGACACGTGTCCACCTGCCGC-3' (3' antisense primer within exon IV)

Results with Baboon Tissues

There was a single band amplified from teh kidney genomic DNA that was cut out of the gel, purified and sequenced. The sequence was 92% identical to the human sequence and the exon-intron boundaries were conserved. The high level of similarity in this intron sequence is notable, because intron sequences are typically not well conserved between species. There was also an in-frame reading sequence within the intron that contained a stop codon, predicting a unique 22 residue carboxyl-terminal tail in the baboon alternatively spliced soluble protein.

The observation that the predicted soluble EPCR isoforms will have unique carboxyl terminal tails provides a structural difference for distinguishing between the isoforms using isoform-specific antibodies. The working model is that plasma levels of proteolyzed soluble EPCR will report endothelial injury, whereas levels of alternatively spliced soluble EPCR will report an endothelial response to stimuli. It is anticipated that the relative plasma levels of the soluble EPCR isoforms will provide information on large vessel endothelial dysfunction and injury in specific pathologies.

Results with Human Tissues

RT-PCR products from human tissues: placenta, lung, and tongue, were electrophoresed using the CRES/CREA primers specific for EPCR. The procedures were the same as used for the baboon tissues. Products corresponding to the membrane isoform of EPCR (mEPCR) and the alternatively-spliced soluble EPCR isoform (sEPCR) were observed. The products look essentially the same as that seen using the baboon tissues. The only difference is that the placental tissue appears to have additional products.

We claim:

1. An assay for soluble endothelial protein C receptor comprising obtaining a sample from a patient to be tested, and measuring the amount of soluble endothelial protein C receptor.

2. The assay of claim 1 wherein the sample is selected from the group consisting of urine, plasma, serum, tissue samples, and interstitial fluid.

3. The assay of claim 1 further comprising the step of correlating the amount of soluble endothelial protein C receptor with calibration standards.

4. The assay of claim 1 wherein the patient has a disorder or disease selected from the group consisting of coagulation and inflammatory states and disorders, disorders or diseases involving damage to endothelium, and large blood vessel disease.

5. The assay of claim 4 wherein the disorder or disease is selected from the group consisting of autoimmune diseases, transplantation, sepsis, shock, pre-eclampsia, diabetes, vascular disease, kidney disease and liver disease.

6. The assay of claim 5 wherein the vascular disease is selected from the group consisting of cardiopulmonary bypass, unstable angina, restenosis, and angioplasty.

7. The assay of claim 1 to detect damage to large blood vessels.

8. A kit for detection and measurement of endothelial protein C receptor comprising an antibody immunoreactive with endothelial protein C receptor, reagents to detect a reaction between the antibody and endothelial protein C receptor in a sample from a patient, and standards to correlate the amount of reaction to normal and abnormal levels of endothelial protein C receptor.

9. The kit of claim 8 where the antibody has a higher affinity for endothelial protein C receptor including the transmembrane domain than for endothelial protein C receptor not including the transmembrane domain.

10. The kit of claim 8 wherein the antibody is immunoreactive with the insert in an alternatively spliced endothelial protein C receptor.

11. The kit of claim 8 wherein the antibodies block binding of endothelial protein C receptor and activated protein C or protein C.

* * * * *